United States Patent
Rönspeck et al.

(10) Patent No.: US 7,205,382 B2
(45) Date of Patent: Apr. 17, 2007

(54) PEPTIDES, THE PRODUCTION AND USE THEREOF FOR BINDING IMMUNOGLOBULINS

(75) Inventors: Wolfgang Rönspeck, Berlin (DE); Ralf Egner, Berlin (DE); Dirk Winkler, Berlin (DE); Rudolf Kunze, Stegelitz (DE)

(73) Assignee: Fresenius Medical Care Affina GmbH, Berlin (DE)

( * ) Notice: Subject to any disclaimer, the term of this patent is extended or adjusted under 35 U.S.C. 154(b) by 157 days.

(21) Appl. No.: 10/415,665

(22) PCT Filed: Nov. 8, 2001

(86) PCT No.: PCT/EP01/12933

§ 371 (c)(1),
(2), (4) Date: Aug. 8, 2003

(87) PCT Pub. No.: WO02/38592

PCT Pub. Date: May 16, 2002

(65) Prior Publication Data

US 2004/0087765 A1 May 6, 2004

(30) Foreign Application Priority Data

Nov. 8, 2000 (EP) .................. 00124418

(51) Int. Cl.
| | |
|---|---|
| *C07K 2/00* | (2006.01) |
| *C07K 5/12* | (2006.01) |
| *C07K 7/64* | (2006.01) |
| *C07K 7/08* | (2006.01) |
| *C07K 7/04* | (2006.01) |
| *C07K 1/107* | (2006.01) |
| *G01N 33/53* | (2006.01) |
| *G01N 33/543* | (2006.01) |
| *G01N 33/563* | (2006.01) |
| *G01N 33/564* | (2006.01) |
| *C07K 1/00* | (2006.01) |

(52) U.S. Cl. .............. 530/300; 530/317; 530/326; 530/327; 530/333; 530/345; 436/501; 436/506; 436/507; 436/509; 436/513

(58) Field of Classification Search ........... 530/327, 530/300
See application file for complete search history.

(56) References Cited

FOREIGN PATENT DOCUMENTS

| | | |
|---|---|---|
| EP | 1 086 955 A1 | 3/2001 |
| WO | WO 01/45746 A2 | 6/2001 |

OTHER PUBLICATIONS

J Rudinger. In: Peptide Hormones, JA Parsons, Ed. (1976), 1-7.*
J. Kyte. "Immunochemical probes of structure" in Structure in Protein Chemistry. (1995), pp. 379-391.*
DeLano et al., "Convergent Solutions to Binding at a Protein—Protein Interface", Science, 287, (2000), 1279-1283.
Krook et al., "Novel peptides binding to the Fc-portion of immunoglobulins obtained from a combinatorial phage display peptide library", Journal of Immunological Methods, 221, (1998), 151-157.

* cited by examiner

*Primary Examiner*—Cecilla J. Tsang
*Assistant Examiner*—Andrew D. Kosar
(74) *Attorney, Agent, or Firm*—Jacobson Holman PLLC

(57) ABSTRACT

Peptides having the following amino acid sequence as well as peptides or proteins which contain this amino acid sequence:

Figure 1:
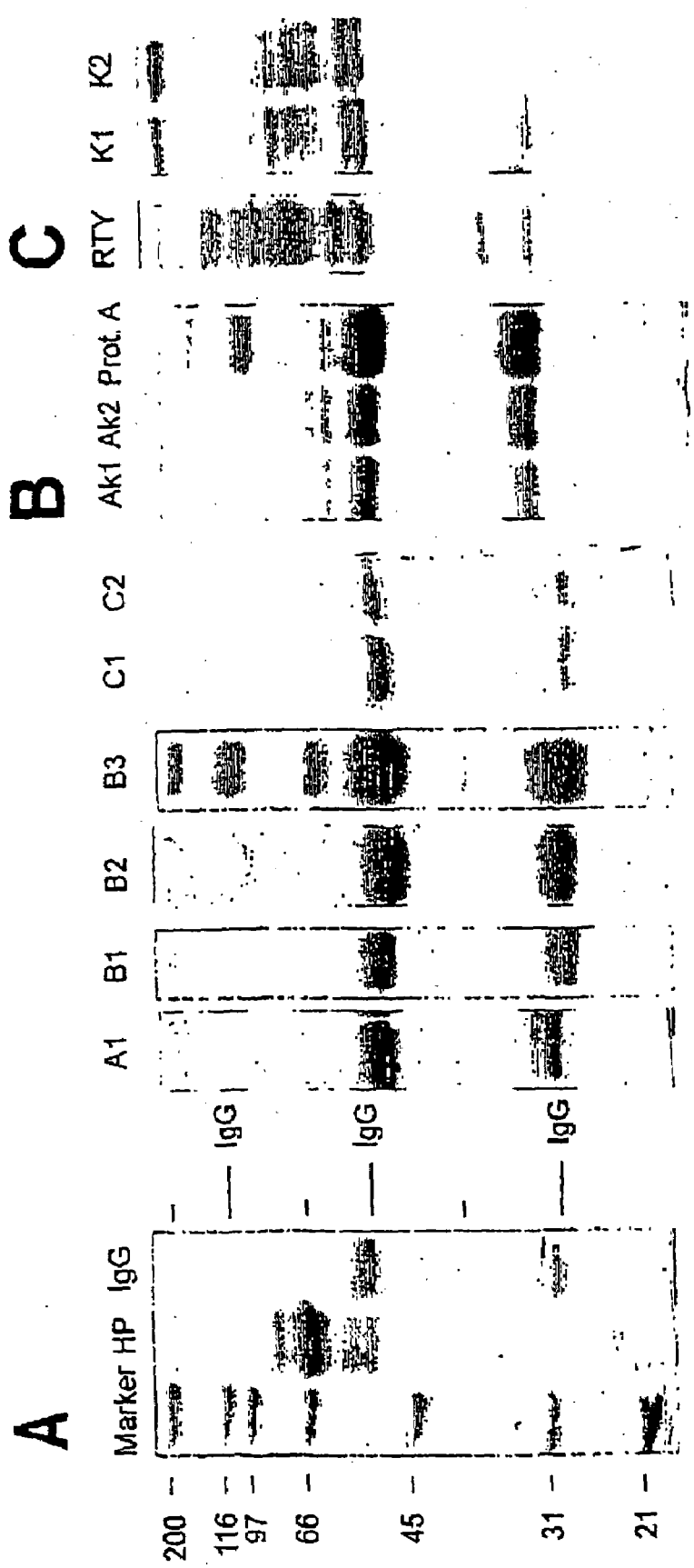

$R^1$-X01-X02-X03-X04-X05-X06-X07-X08-X09-X10-X11-X12-X13-$R^2$.

These peptides have a high affinity for immunoglobulins. Applications of the peptides according to the invention are also described.

21 Claims, 2 Drawing Sheets

SEQUENCE LISTING

```
<160> NUMBER OF SEQ ID NOS: 88

<210> SEQ ID NO 1
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 1

Ala Cys Ala Trp His Leu Gly Lys Leu Val Trp Cys Thr
 1               5                  10

<210> SEQ ID NO 2
<211> LENGTH: 13
<212> TYPE: PRT
<213> ORGANISM: Artificial sequence
```

```
<220> FEATURE:
<223> OTHER INFORMATION: Description of the artificial sequence:
      synthetic peptide having affinity for
      immunoglobulins

<400> SEQUENCE: 2

Glu Cys Ala Trp His Leu Gly Lys Leu Val Trp Cys Thr
 1               5                  10

<210> SEQ ID NO 3
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 3

Gly Cys Ala Trp His Leu Gly Lys Leu Val Trp Cys Thr
 1               5                  10

<210> SEQ ID NO 4
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 4

Cys Ala Trp His Leu Gly Lys Leu Val Trp Cys Thr
 1               5                  10

<210> SEQ ID NO 5
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 5

Asp Ser Ala Trp His Leu Gly Lys Leu Val Trp Cys Thr
 1               5                  10

<210> SEQ ID NO 6
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 6

Asp Cys Ser Trp His Leu Gly Lys Leu Val Trp Cys Thr
 1               5                  10

<210> SEQ ID NO 7
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins
```

-continued

<400> SEQUENCE: 7

Asp Cys Thr Trp His Leu Gly Lys Leu Val Trp Cys Thr
1               5                   10

<210> SEQ ID NO 8
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 8

Asp Cys Ala Glu His Leu Gly Lys Leu Val Trp Cys Thr
1               5                   10

<210> SEQ ID NO 9
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 9

Asp Cys Ala Phe His Leu Gly Lys Leu Val Trp Cys Thr
1               5                   10

<210> SEQ ID NO 10
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 10

Asp Cys Ala His His Leu Gly Lys Leu Val Trp Cys Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 11

Asp Cys Ala Lys His Leu Gly Lys Leu Val Trp Cys Thr
1               5                   10

<210> SEQ ID NO 12
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 12

Asp Cys Ala Met His Leu Gly Lys Leu Val Trp Cys Thr

<210> SEQ ID NO 13
<211> LENGTH: 13
<212> TYPE: PRT
<213> ORGANISM: Artificial sequence
<220> FEATURE:
<223> OTHER INFORMATION: Description of the artificial sequence:
synthetic peptide having affinity for
immunoglobulins

<400> SEQUENCE: 13

Asp Cys Ala Arg His Leu Gly Lys Leu Val Trp Cys Thr
 1               5                  10

<210> SEQ ID NO 14
<211> LENGTH: 13
<212> TYPE: PRT
<213> ORGANISM: Artificial sequence
<220> FEATURE:
<223> OTHER INFORMATION: Description of the artificial sequence:
synthetic peptide having affinity for
immunoglobulins

<400> SEQUENCE: 14

Asp Cys Ala Ser His Leu Gly Lys Leu Val Trp Cys Thr
 1               5                  10

<210> SEQ ID NO 15
<211> LENGTH: 13
<212> TYPE: PRT
<213> ORGANISM: Artificial sequence
<220> FEATURE:
<223> OTHER INFORMATION: Description of the artificial sequence:
synthetic peptide having affinity for
immunoglobulins

<400> SEQUENCE: 15

Asp Cys Ala Thr His Leu Gly Lys Leu Val Trp Cys Thr
 1               5                  10

<210> SEQ ID NO 16
<211> LENGTH: 13
<212> TYPE: PRT
<213> ORGANISM: Artificial sequence
<220> FEATURE:
<223> OTHER INFORMATION: Description of the artificial sequence:
synthetic peptide having affinity for
immunoglobulins

<400> SEQUENCE: 16

Asp Cys Ala Val His Leu Gly Lys Leu Val Trp Cys Thr
 1               5                  10

<210> SEQ ID NO 17
<211> LENGTH: 13
<212> TYPE: PRT
<213> ORGANISM: Artificial sequence
<220> FEATURE:
<223> OTHER INFORMATION: Description of the artificial sequence:
synthetic peptide having affinity for
immunoglobulins

<400> SEQUENCE: 17

Asp Cys Ala Trp His Leu Gly Lys Leu Val Trp Cys Thr
 1               5                  10

<210> SEQ ID NO 18

```
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 18

Asp Cys Ala Tyr His Leu Gly Lys Leu Val Trp Cys Thr
  1               5                  10

<210> SEQ ID NO 19
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 19

Asp Cys Ala Trp His Asp Gly Lys Leu Val Trp Cys Thr
  1               5                  10

<210> SEQ ID NO 20
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 20

Asp Cys Ala Trp His Glu Gly Lys Leu Val Trp Cys Thr
  1               5                  10

<210> SEQ ID NO 21
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 21

Asp Cys Ala Trp His Gly Gly Lys Leu Val Trp Cys Thr
  1               5                  10

<210> SEQ ID NO 22
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 22

Asp Cys Ala Trp His His Gly Lys Leu Val Trp Cys Thr
  1               5                  10

<210> SEQ ID NO 23
<211> LENGTH: 13
<212> TYPE: PRT
<213> ORGANISM: Artificial sequence
<220> FEATURE:
```

<223> OTHER INFORMATION: Description of the artificial sequence:
      synthetic peptide having affinity for
      immunoglobulins

<400> SEQUENCE: 23

Asp Cys Ala Trp His Lys Gly Lys Leu Val Trp Cys Thr
 1               5                  10

<210> SEQ ID NO 24
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 24

Asp Cys Ala Trp His Met Gly Lys Leu Val Trp Cys Thr
 1               5                  10

<210> SEQ ID NO 25
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 25

Asp Cys Ala Trp His Asn Gly Lys Leu Val Trp Cys Thr
 1               5                  10

<210> SEQ ID NO 26
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 26

Asp Cys Ala Trp His Gln Gly Lys Leu Val Trp Cys Thr
 1               5                  10

<210> SEQ ID NO 27
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 27

Asp Cys Ala Trp His Arg Gly Lys Leu Val Trp Cys Thr
 1               5                  10

<210> SEQ ID NO 28
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

```
<400> SEQUENCE: 28

Asp Cys Ala Trp His Leu Asp Lys Leu Val Trp Cys Thr
 1               5                  10

<210> SEQ ID NO 29
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 29

Asp Cys Ala Trp His Leu Gly Asp Leu Val Trp Cys Thr
 1               5                  10

<210> SEQ ID NO 30
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 30

Asp Cys Ala Trp His Leu Gly His Leu Val Trp Cys Thr
 1               5                  10

<210> SEQ ID NO 31
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 31

Asp Cys Ala Trp His Leu Gly Lys Leu Val Trp Cys Thr
 1               5                  10

<210> SEQ ID NO 32
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 32

Asp Cys Ala Trp His Leu Gly Met Leu Val Trp Cys Thr
 1               5                  10

<210> SEQ ID NO 33
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 33

Asp Cys Ala Trp His Leu Gly Asn Leu Val Trp Cys Th

<210> SEQ ID NO 34
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 34

Asp Cys Ala Trp His Leu Gly Gln Leu Val Trp Cys Thr
 1               5                  10

<210> SEQ ID NO 35
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 35

Asp Cys Ala Trp His Leu Gly Arg Leu Val Trp Cys Thr
 1               5                  10

<210> SEQ ID NO 36
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 36

Asp Cys Ala Trp His Leu Gly Lys Lys Val Trp Cys Thr
 1               5                  10

<210> SEQ ID NO 37
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 37

Asp Cys Ala Trp His Leu Gly Lys Arg Val Trp Cys Thr
 1               5                  10

<210> SEQ ID NO 38
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 38

Asp Cys Ala Trp His Leu Gly Lys Leu Val Trp Ser Thr
 1               5                  10

<210> SEQ ID NO 39
<211> LENGTH: 13

```
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 39

Asp Cys Ala Trp His Leu Gly Lys Leu Val Trp Cys Asp
 1               5                  10

<210> SEQ ID NO 40
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 40

Asp Cys Ala Trp His Leu Gly Lys Leu Val Trp Cys Glu
 1               5                  10

<210> SEQ ID NO 41
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 41

Asp Cys Ala Trp His Leu Gly Lys Leu Val Trp Cys Lys
 1               5                  10

<210> SEQ ID NO 42
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 42

Asp Cys Ala Trp His Leu Gly Lys Leu Val Trp Cys Gln
 1               5                  10

<210> SEQ ID NO 43
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 43

Asp Cys Ala Trp His Leu Gly Lys Leu Val Trp Cys Arg
 1               5                  10

<210> SEQ ID NO 44
<211> LENGTH: 13
<212> TYPE: PRT
<213> ORGANISM: Artificial sequence
<220> FEATURE:
<223> OTHER INFORMATION: Description of the artificial sequence:
```

```
      synthetic peptide having affinity for
      immunoglobulins

<400> SEQUENCE: 44

Asp Cys Ala Trp His Leu Gly Lys Leu Val Trp Cys Ser
 1               5                  10

<210> SEQ ID NO 45
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 45

Asp Cys Ala Trp His Leu Gly Lys Leu Val Trp Cys
 1               5                  10

<210> SEQ ID NO 46
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 46

Cys Ala Trp His Leu Gly Lys Leu Val Trp Cys Thr
 1               5                  10

<210> SEQ ID NO 47
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 47

Asp Cys Ala Trp His Leu Gly Lys Leu Val Trp Cys
 1               5                  10

<210> SEQ ID NO 48
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 48

Cys Ala Trp His Leu Gly Lys Leu Val Trp Cys
 1               5                  10

<210> SEQ ID NO 49
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 49
```

Asp Cys Ser Trp His Leu Gly Lys Leu Val Trp Cys Thr
 1               5                  10

<210> SEQ ID NO 50
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 50

Asp Cys Ala Trp His His Gly Lys Leu Val Trp Cys Thr
 1               5                  10

<210> SEQ ID NO 51
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 51

Asp Cys Ala Trp His Gln Gly Lys Leu Val Trp Cys Thr
 1               5                  10

<210> SEQ ID NO 52
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 52

Asp Cys Ala Trp His Gly Gly Lys Leu Val Trp Cys Thr
 1               5                  10

<210> SEQ ID NO 53
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 53

Asp Cys Ala Trp His Gly Gly Lys Leu Val Trp Cys Thr
 1               5                  10

<210> SEQ ID NO 54
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 54

Asp Cys Ala Trp His Gly Gly His Leu Val Trp Cys Thr
 1               5                  10

```
<210> SEQ ID NO 55
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 55

Asp Cys Ala Trp His Gly Gly Lys Leu Val Trp Cys Glu
  1               5                  10

<210> SEQ ID NO 56
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 56

Asp Cys Ala Trp His Leu Gly Lys Leu Val Trp Cys Thr
  1               5                  10

<210> SEQ ID NO 57
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 57

Asp Cys Ala Trp His Gln Gly Lys Leu Val Trp Cys Thr
  1               5                  10

<210> SEQ ID NO 58
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 58

Asp Cys Ala Tyr His Leu Gly Lys Leu Val Trp Cys Thr
  1               5                  10

<210> SEQ ID NO 59
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 59

Asp Cys Ser Trp His Leu Gly Lys Leu Val Trp Cys Thr
  1               5                  10

<210> SEQ ID NO 60
<211> LENGTH: 13
<212> TYPE: PRT
```

<213> ORGANISM: Artificial sequence
<220> FEATURE:
<223> OTHER INFORMATION: Description of the artificial sequence: synthetic peptide having affinity for immunoglobulins

<400> SEQUENCE: 60

Asp Cys Ala Tyr His Gln Gly Lys Leu Val Trp Cys Thr
 1               5                  10

<210> SEQ ID NO 61
<211> LENGTH: 13
<212> TYPE: PRT
<213> ORGANISM: Artificial sequence
<220> FEATURE:
<223> OTHER INFORMATION: Description of the artificial sequence: synthetic peptide having affinity for immunoglobulins

<400> SEQUENCE: 61

Asp Cys Ser Trp His Gln Gly Lys Leu Val Trp Cys Thr
 1               5                  10

<210> SEQ ID NO 62
<211> LENGTH: 13
<212> TYPE: PRT
<213> ORGANISM: Artificial sequence
<220> FEATURE:
<223> OTHER INFORMATION: Description of the artificial sequence: synthetic peptide having affinity for immunoglobulins

<400> SEQUENCE: 62

Asp Cys Ser Tyr His Leu Gly Lys Leu Val Trp Cys Thr
 1               5                  10

<210> SEQ ID NO 63
<211> LENGTH: 13
<212> TYPE: PRT
<213> ORGANISM: Artificial sequence
<220> FEATURE:
<223> OTHER INFORMATION: Description of the artificial sequence: synthetic peptide having affinity for immunoglobulins

<400> SEQUENCE: 63

Asp Cys Ser Tyr His Gln Gly Lys Leu Val Trp Cys Thr
 1               5                  10

<210> SEQ ID NO 64
<211> LENGTH: 12
<212> TYPE: PRT
<213> ORGANISM: Artificial sequence
<220> FEATURE:
<223> OTHER INFORMATION: Description of the artificial sequence: synthetic peptide having affinity for immunoglobulins

<400> SEQUENCE: 64

Cys Ala Trp His Leu Gly Lys Leu Val Trp Cys Thr
 1               5                  10

<210> SEQ ID NO 65
<211> LENGTH: 12
<212> TYPE: PRT
<213> ORGANISM: Artificial sequence
<220> FEATURE:
<223> OTHER INFORMATION: Description of the artificial sequence: synthetic peptide having affinity for -continued

```
      immunoglobulins

<400> SEQUENCE: 65

Cys Ala Trp His Gln Gly Lys Leu Val Trp Cys Thr
 1               5                  10

<210> SEQ ID NO 66
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 66

Cys Ala Tyr His Leu Gly Lys Leu Val Trp Cys Thr
 1               5                  10

<210> SEQ ID NO 67
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 67

Cys Ser Trp His Leu Gly Lys Leu Val Trp Cys Thr
 1               5                  10

<210> SEQ ID NO 68
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 68

Cys Ala Tyr His Gln Gly Lys Leu Val Trp Cys Thr
 1               5                  10

<210> SEQ ID NO 69
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 69

Cys Ser Trp His Gln Gly Lys Leu Val Trp Cys Thr
 1               5                  10

<210> SEQ ID NO 70
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 70
```

Cys Ser Tyr His Leu Gly Lys Leu Val Trp Cys Thr
1               5                  10

<210> SEQ ID NO 71
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 71

Cys Ser Tyr His Gln Gly Lys Leu Val Trp Cys Thr
1               5                  10

<210> SEQ ID NO 72
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 72

Asp Cys Ala Trp His Leu Gly Lys Leu Val Trp Cys
1               5                  10

<210> SEQ ID NO 73
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 73

Asp Cys Ala Trp His Gln Gly Lys Leu Val Trp Cys
1               5                  10

<210> SEQ ID NO 74
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 74

Asp Cys Ala Tyr His Leu Gly Lys Leu Val Trp Cys
1               5                  10

<210> SEQ ID NO 75
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 75

Asp Cys Ser Trp His Leu Gly Lys Leu Val Trp Cys
1               5                  10

```
<210> SEQ ID NO 76
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 76

Asp Cys Ala Tyr His Gln Gly Lys Leu Val Trp Cys
 1               5                  10

<210> SEQ ID NO 77
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 77

Asp Cys Ser Trp His Gln Gly Lys Leu Val Trp Cys
 1               5                  10

<210> SEQ ID NO 78
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 78

Asp Cys Ser Tyr His Leu Gly Lys Leu Val Trp Cys
 1               5                  10

<210> SEQ ID NO 79
<211> LENGTH: 12
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 79

Asp Cys Ser Tyr His Gln Gly Lys Leu Val Trp Cys
 1               5                  10

<210> SEQ ID NO 80
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 80

Cys Ala Trp His Leu Gly Lys Leu Val Trp Cys
 1               5                  10

<210> SEQ ID NO 81
<211> LENGTH: 11
<212> TYPE: PRT
<213> ORGANISM: Artificial sequence
```

```
<220> FEATURE:
<223> OTHER INFORMATION: Description of the artificial sequence:
      synthetic peptide having affinity for
      immunoglobulins

<400> SEQUENCE: 81

Cys Ala Trp His Gln Gly Lys Leu Val Trp Cys
 1               5                  10

<210> SEQ ID NO 82
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 82

Cys Ala Tyr His Leu Gly Lys Leu Val Trp Cys
 1               5                  10

<210> SEQ ID NO 83
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 83

Cys Ser Trp His Leu Gly Lys Leu Val Trp Cys
 1               5                  10

<210> SEQ ID NO 84
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 84

Cys Ala Tyr His Gln Gly Lys Leu Val Trp Cys
 1               5                  10

<210> SEQ ID NO 85
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 85

Cys Ser Trp His Gln Gly Lys Leu Val Trp Cys
 1               5                  10

<210> SEQ ID NO 86
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins
```

```
<400> SEQUENCE: 86

Cys Ser Tyr His Leu Gly Lys Leu Val Trp Cys
 1               5                   10

<210> SEQ ID NO 87
<211> LENGTH: 11
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 87

Cys Ser Tyr His Gln Gly Lys Leu Val Trp Cys
 1               5                   10

<210> SEQ ID NO 88
<211> LENGTH: 13
<212> TYPE: PRT
<213> ORGANISM: Artificial sequence
<220> FEATURE:
<223> OTHER INFORMATION: Description of the artificial sequence:
      synthetic peptide having affinity for
      immunoglobulins

<400> SEQUENCE: 88

Asp Cys Ala Trp His Leu Gly Glu Leu Val Trp Cys Thr
 1               5                   10
```

PEPTIDES, THE PRODUCTION AND USE THEREOF FOR BINDING IMMUNOGLOBULINS

This is a 371 of PCT/EP01/12933, filed Nov. 8, 2001, and published in German.

The present invention relates to peptides having affinity for immunoglobulins, solid phases to which the peptides according to the invention are bound, a method for the adsorption of immunoglobulins, a device for performing the method, and uses of the peptides according to the invention.

Immunoglobulins are protein molecules which occur in all vertebrates and which serve for the body's specific immune defense by binding to antigens, microbial and other exogenous structures and neutralize them. Antigen-bearing structures, such as bacteria or parasites which have intruded into the body as well as virus-infected body cells, are tagged by bound immunoglobulins for destruction by correspondingly specialized cells or molecular systems, such as the complement to system. Depending on the structure of their molecular subunits, immunoglobulins are subdivided into different immunoglobulin classes, which are also distinct with respect to their biological activities, such as the capability of complement activation or mucosa permeability. In general, all immunoglobulins are distinct by their variable binding sites specific for the respective antigen, irrespective of the class of immunoglobulins. All immunoglobulins have common structural features through which they may also be bound commonly, for which the molecular subunit called the "Fc region" is preferred (Davies and Metzger (1983); Alt et al. (1987)).

Immunoglobulin-binding molecules which occur in nature are mainly surface receptors of body cells which recognize the FC region of the different immunoglobulins and bind to them. After the receptors have bound immunoglobulins, different activation processes are triggered through them, depending on the class of the bound immunoglobulin and the cell type (McKenzie and Schreiber (1994); Makiya and Stigbrand (1992); Sarfati et al. (1992); Capron et al. (1992); Shen (1992); Sandor et al. (1992)).

In addition to surface receptors, molecules of the complement system also bind to the Fc region of immunoglobulins. The complement system is a system of mutually matched proteins which serves for the destruction of the antigen-bearing target structure and has two different paths of activation. In one of them, the classical path, activation is effected through the binding of the complement component C1 or its subunit C1q to the Fc region of the antigen-bound immunoglobulins (Miletic and Frank (1995)).

Some bacteria also have developed proteins which are capable of binding immunoglobulins through the Fc region. These include protein A of the staphylococci and protein G of the streptococci. These proteins and their derivatives are interesting tools in immunological research, for example, in the study of receptor-immunoglobulin interaction, and when coupled to a support matrix, they are widely used in the purification of immunoglobulins by affinity chromatography (Stahl et al. (1993)).

Proceeding from this application, therapeutic immunapheresis was established for the treatment of autoimmune diseases. In this process, immunoglobulins are removed from human plasma by means of matrix-coupled protein A, and thus the concentration of pathogenic auto-antibodies is decreased (Belak et al. (1994)).

Currently, there are two commercially available protein A products which are distinct with respect to the adsorber matrix employed. On the one hand, protein A immobilized on agarose (sepharose) is used as the support matrix (Immunosorba, Fresenius HemoCare AG, Germany) (Samuelsson (1998)); on the other hand, silica gel is employed as the support matrix (Prosorba, Cypress Bioscience Inc., USA). The use of immunapheresis with protein A for removing the immunoglobulins was successfully employed in different autoimmune diseases, for example, rheumatoid arthritis (Felson et al. (1999)).

Further, after immunization with immunoglobulins of a particular species, antibodies can be induced in another species which are then capable of binding the immunoglobulins of the first species. Based on this principle is a product for therapeutic immunapheresis which uses matrix-coupled antibodies from sheep which are obtained from the serum of the animals upon immunization with human immunoglobulins. This system (Ig-Therasorb, PlasmaSelect AG, Germany) is also employed in the total immunoglobulin removal and thus also serves for the therapeutic removal of pathogenic antibodies (Koll (1998)), for example, of inhibitors of factor VIII and factor IX (Knobl and Derfler (1999)).

Matrix-immobilized amino acids are also employed for therapeutic immun-apheresis. For this purpose, adsorbers based on phenylalanine (IM-PH350, Asahi Medical Co. Ltd., Japan) and tryptophan (IM-TR350, Asahi, Japan) are employed (Jimenez et al. (1993); Fadul et al. (1996)). However, the binding capability of these adsorbers is not limited to immunoglobulins, in contrast to the adsorber systems mentioned above, but other proteins, such as fibrinogen, which is necessary for clotting, are also removed from the blood plasma.

A completely different binding principle is employed in the use of peptides as antigens or antigen mimetics for removing pathogenic auto-antibodies. For example, the adsorber MG-50 (Kuraray Co. Ltd., Japan) is employed for the elimination of auto-antibodies against acetylcholine receptor in the treatment of myasthenia gravis (Takamori and Ide (1996)). Another example is the specific immunapheretic elimination of auto-antibodies against $\beta1$-adrenergic receptor (EP 99 118 631, Affina Immuntechnik GmbH, Germany) in the therapy of dilatative cardiomyopathy (DCM). That is to say, in the examples mentioned, only those immunoglobulins are removed which are directed against the respective peptide antigen, whereas all other immunoglobulins are not bound. The use of peptides for the binding of selected immunoglobulins through their antigen-binding site is state of the art.

Interestingly and in contrast to the peptides described above, the literature has also described peptides which are not bound through the antigen-binding site of an immunoglobulin, but to the Fc region of immunoglobulins. Thus, a protein-A-mimetic peptide has been described which is suitable for the technical purification of immunoglobulins (Fassina et al. (1996); Fassina et al. (1998)). Further, a peptide has been described which binds a monoclonal IgG antibody in the region of the protein A binding site of the immunoglobulin in a buffered solution (DeLano et al. (2000) as well as WO-A-01/45746). Other peptides which also bind in the Fc region and consists of 10 amino acids were described by the Krook group of workers (Krook et al. (1998)).

For the therapeutic suitability as a pharmaceutical agent and/or for the therapeutic use in medical engineering of molecules for the binding of immunoglobulins of classes $G_{1-4}$, A and M, the specificity for the mentioned classes of immunoglobulins, a low binding of other plasma components and the stability of the peptide in body fluids, such as human plasma or serum, are elementary preconditions.

Thus, it is the object of the invention to provide novel peptides which have a high affinity for immunoglobulins.

According to the invention, this object is achieved by synthetic peptides which preferably bind selectively to immunoglobulins, especially of classes $G_{1-4}$, A and M in complex solutions, such as body fluids and native human blood plasma, and are stable under such conditions of use.

The peptides claimed in this patent surprisingly meet the requirements mentioned both in a soluble form and in an immobilized state and are thus suitable for medical-technical and pharmacological use.

Especially upon immobilization of the peptides through X08=K (Lys) (see below), the peptides meet the mentioned requirements, surprisingly also after thermal treatment (autoclavation at 121° C.).

In detail, these are the peptides according to the invention having the following amino acid sequence as well as peptides or proteins containing this amino acid sequence:

$R^1$—X01-X02-X03-X04-X05-X06-X07-X08-X09-X10-X11-X12-X13-$R^2$, wherein $R^1$, $R^2$ as well as X01 to X013 have the following meanings:
$R^1$=amino, acetyl as well as spacer/linker, or deletion
X01=A, D, E, G, deletion
X02=C, S, D, E, diaminobutyric acid (Dab), diaminopropionic acid (Dpr), K, ornithine (Orn),
X03=A, S, T
X04=E, F H, K, M, R, S, T, V, W, Y
X05=H
X06=G, H, K, L, M, N, Q, R
X07=D, G
X08=D, H, K, M, N, Q, R
X09=K, L, R
X10=V
X11=W
X12=C, S, D, E, diaminobutyric acid (Dab), diaminopropionic acid (Dpr), K, ornithine (Orn),
X13=D, E, K, Q, R, S, T, deletion
$R^2$=—COOH, -amide, -GK, -GKK, -(βA)GK, -(βA)GKK, -(βA)(βA), -(βA)(βA)K as well as spacer/linker, or deletion.

The peptides according to the invention may be, in particular, in a linear as well as cyclic form, wherein the peptide ring closure is effected through disulfide bridging when two cysteines are present, or through amide cyclization which is optionally effected through side chains, through the C and N termini or through a combination of these two possibilities.

According to the invention, the following peptides are preferred:

R1-ACAWHLGKLVWCT-R2

R1-ECAWHLGKLVWCT-R2

R1-GCAWHLGKLVWCT-R2

R1-CAWHLGKLVWCT-R2 with a maximum of four simultaneous amino acid exchanges in the peptide positions as follows:
X02=S
X03=S, T
X04=E, F, H, K, M, R, S, T, V, Y
X06=G, H K, M, N, Q, R
X07=D
X08=D, H, M, N, Q, R
X09=K, R
X12=S
X13=D, E, K, Q, R, S, deletion
or

R1-DSAWHLGKLVWCT-R2 with a maximum of four simultaneous amino acid exchanges in the peptide positions as follows:
X01=A, E, G, deletion
X03=S, T
X04=E, F, H, K, M, R, S, T, V, Y
X06=G, H, K, M, N, Q, R
X07=D
X08=D, H, M, N, Q, R
X09=K, R
X12=S
X13=D, E, K, Q, R, S, deletion
or According to the invention, the following peptides are preferred:

R1-ACAWHLGKLVWCT-R2 (SEQ ID NO: 1)

R1-ECAWHLGKLVWCT-R2 (SEQ ID NO: 2)

R1-GCAWHLGKLVWCT-R2 (SEQ ID NO: 3)

R1-CAWHLGKLVWCT-R2 (SEQ ID NO: 4)

with a maximum of four simultaneous amino acid exchanges in the peptide positions as follows:
X02=S
X03=S, T
X04=E, F, H, K, M, R, S, T, V, Y
X06=G, H, K, M, N, Q, R
X07=D
X08=D, H, M, N, Q, R
X09=K, R
X12=S
X13=D, E, K, Q, R, S, deletion
or

R1-DSAWHLGKLVWCT-R2 (SEQ ID NO: 5)

with a maximum of four simultaneous amino acid exchanges in the peptide positions as follows:
X01=A, E, G, deletion
X03=S, T
X04=E, F, H, K, M, R, S, T, V, Y
X06=G, H, K, M, N, Q, R
X07=D
X08=D, H, M, N, Q, R
X09=K, R
X12=S
X13=D, E, K, Q, R, S, deletion
or

R1-DCSWHLGKLVWCT-R2 (SEQ ID NO: 6)

R1-DCTWHLGKLVWCT-R2 (SEQ ID NO: 7)

with a maximum of four simultaneous amino acid exchanges in the peptide positions as follows:
X01=A, E, G, deletion
X02=S X04=E, F, H, K, M, R, S, T, V, Y
X06=G, H, K, M, N, Q, R
X07=D
X08=D, H, M, N, Q, R
X09=K, R
X12=S
X13=D, E, K, Q, R, S, deletion,
or

R1-DCAEHLGKLVWCT-R2 (SEQ ID NO: 8)

R1-DCAFHLGKLVWCT-R2 (SEQ ID NO: 9)

R1-DCAHHLGKLVWCT-R2 (SEQ ID NO: 10)

R1-DCAKHLGKLVWCT-R2 (SEQ ID NO: 11)

R1-DCAMHLGKLVWCT-R2 (SEQ ID NO: 12)

R1-DCARHLGKLVWCT-R2 (SEQ ID NO: 13)

R1-DCASHLGKLVWCT-R2 (SEQ ID NO: 14)

R1-DCATHLGKLVWCT-R2 (SEQ ID NO: 15)

R1-DCAVHLGKLVWCT-R2 (SEQ ID NO: 16)

R1-DCAWHLGKLVWCT-R2 (SEQ ID NO: 17)

R1-DCAYHLGKLVWCT-R2 (SEQ ID NO: 18)

with a maximum of four simultaneous amino acid exchanges in the peptide positions as follows:
X01=A, E, G, deletion
X02=S
X03=S, T
X06=G, H, K, M, N, Q, R
X07=D
X08=D, H, M, N, Q, R
X09=K, R
X12=S
X13=D, E, K, Q, R, S, deletion,
or

R1-DCAWHDGKLVWCT-R2 (SEQ ID NO: 19)

R1-DCAWHEGKLVWCT-R2 (SEQ ID NO: 20)

R1-DCAWHGGKLVWCT-R2 (SEQ ID NO: 21)

R1-DCAWHHGKLVWCT-R2 (SEQ ID NO: 22)

R1-DCAWHKGKLVWCT-R2 (SEQ ID NO: 23)

R1-DCAWHMGKLVWCT-R2 (SEQ ID NO: 24)

R1-DCAWHNGKLVWCT-R2 (SEQ ID NO: 25)

R1-DCAWHQGKLVWCT-R2 (SEQ ID NO: 26)

R1-DCAWHRGKLVWCT-R2 (SEQ ID NO: 27)

with a maximum of four simultaneous amino acid exchanges in the peptide positions as follows:
X01=A, E, G, deletion
X02=S
X03=S, T
X04=E, F, H, K, M, R, S, T, V, Y
X07=D
X08=D, H, M, N, Q, R
X09=K, R X12=S
X13=D, E, K, Q, R, S, deletion,
or

R1-DCAWHLDKLVWCT-R2 (SEQ ID NO: 28)

with a maximum of four simultaneous amino acid exchanges in the peptide positions as follows:
X01=A, E, G, deletion
X02=S
X03=S, T
X04=E, F, H, K, M, R, S, T, V, Y
X06=G, H, K, M, N, Q, R
X08=D, H, M, N, Q, R
X09=K, R
X12=S
X13=D, E, K, Q, R, S, deletion
or

R1-DCAWHLGDLVWCT-R2 (SEQ ID NO: 29)

R1-DCAWHLGHLVWCT-R2 (SEQ ID NO: 30)

R1-DCAWHLGKLVWCT-R2 (SEQ ID NO: 31)

R1-DCAWHLGMLVWCT-R2 (SEQ ID NO: 32)

R1-DCAWHLGNLVWCT-R2 (SEQ ID NO: 33)

R1-DCAWHLGQLVWCT-R2 (SEQ ID NO: 34)

R1-DCAWHLGRLVWCT-R2 (SEQ ID NO: 35)

with a maximum of four simultaneous amino acid exchanges in the peptide positions as follows:
X01=A, E, G, deletion
X02=S
X03=S, T
X04=E, F, H, K, M, R, S, T, V, Y
X06=G, H, K, M, N, Q, R
X07=D
X09=K, R
X12=S
X13=D, E, K, Q, R, S, deletion,
or

R1-DCAWHLGKKVWCT-R2 (SEQ ID NO: 36)

R1-DCAWHLGKRVWCT-R2 (SEQ ID NO: 37)

with a maximum of four simultaneous amino acid exchanges in the peptide positions as follows:
X01=A, E, G, deletion
X02=S
X03=S, T
X04=E, F, H, K, M, R, S, T, V, Y
X06=G, H, K, M, N, Q, R
X07=D
X08=D, H, M, N, Q, R
X12=S
X13=D, E, K, Q, R, S, deletion,
or

R1-DCAWHLGKLVWST-R2 (SEQ ID NO: 38)

with a maximum of four simultaneous amino acid exchanges in the peptide positions as follows:
X01=A, E, G, deletion
X02=S
X03=S, T
X04=E, F, H, K, M, R, S, T, V, Y
X06=G, H, K, M, N, Q, R
X07=D X08=D, H, M, N, Q, R
X09=K, R
X13=D, E, K, Q, R, S, deletion
or

R1-DCAWHLGKLVWCD-R2 (SEQ ID NO: 39)

R1-DCAWHLGKLVWCE-R2 (SEQ ID NO: 40)

R1-DCAWHLGKLVWCK-R2 (SEQ ID NO: 41)

R1-DCAWHLGKLVWCQ-R2 (SEQ ID NO: 42)

R1-DCAWHLGKLVWCR-R2 (SEQ ID NO: 43)

R1-DCAWHLGKLVWCS-R2 (SEQ ID NO: 44)

R1-DCAWHLGKLVWC-R2 (SEQ ID NO: 45)

with a maximum of four simultaneous amino acid exchanges in the peptide positions as follows:
X01=A, E, G, deletion
X02=S
X03=S, T
X04=E, F, H, K, M, R, S, T, V, Y
X06=G, H, K, M, N, Q, R
X07=D
X08=D, H, M, N, Q, R
X09=K, R
X12=S
wherein
R1=amino, acetyl as well as spacer/linker,
R2=—COOH, -amide, -GK, -GKK, -(βA)GK, -(βA)GKK (SEQ ID NO: 89), -(βA)(βA), -(βA)(βA)K as well as spacer/linker, the cysteines in positions X02 and X12 are optionally used for a ring closure through disulfide bridging, or the cysteines in positions X02 and X12 are replaced by Dpr or Dab or K or Orn for X02 in combination with D or E for X12 and employed for amide cyclization through the side chains;

or the cysteines in positions X02 and X12 are replaced by D or E for X02 in combination with Dpr or Dab or K or Orn for X12 and employed for amide cyclization through the side chains;

or, when R2=COOH, the position X02 is Dpr or Dab or K or Orn and its side chain forms a ring closure with the C-terminal amino acid through amide cyclization;

or, when R1=NH2, the position X12 is E or D and its side chain forms a ring closure with the N-terminal amino acid through amide cyclization;

or, when R1=NH2 and R2=COOH, the N-terminal and C-terminal amino acids of the peptide are used for ring closure through amide formation;

and any lysines which are not used for ring closure may be derivatized by spacers/linkers. Further, according to the invention, peptides are preferred which have the following peptide sequences and which may be linear or optionally cyclized through the N and C termini of the peptide through amide formation:

R1-CAWHLGKLVWCT-R2 (SEQ ID NO: 46)

R1-DCAWHLGKLVWC-R2 (SEQ ID NO: 47)

R1-CAWHLGKLVWC-R2 (SEQ ID NO: 48)

R1-DCSWHLGKLVWCT-R2 (SEQ ID NO: 49)

R1-DCAWHHGKLVWCT-R2 (SEQ ID NO: 50)

R1-DCAWHQGKLVWCT-R2 (SEQ ID NO: 51)

R1-DCAWHGGKLVWCT-R2 (SEQ ID NO: 52)

R1-DCAWRGGKLVWCT-R2 (SEQ ID NO: 53)

R1-DCAWHGGHLVWCT-R2 (SEQ ID NO: 54)

R1-DCAWHGGKLVWCE-R2 (SEQ ID NO: 55)

wherein R1=amino, acetyl and
R2=—COOH, -amide, -GK, -GKK, -(βA)GK, -(βA)GKK (SEQ ID NO: 89), -(βA)(βA),

R1-DCAWHLGKLVWCT-R2 (SEQ ID NO: 56)

R1-DCAWHQGKLVWCT-R2 (SEQ ID NO: 57)

R1-DCAYHLGKLVWCT-R2 (SEQ ID NO: 58)

R1-DCSWHLGKLVWCT-R2 (SEQ ID NO: 59)

R1-DCAYHQGKLVWCT-R2 (SEQ ID NO: 60)

R1-DCSWHQGKLVWCT-R2 (SEQ ID NO: 61)

R1-DCSYHLGKLVWCT-R2 (SEQ ID NO: 62)

R1-DCSYHQGKLVWCT-R2 (SEQ ID NO: 63)

R1-CAWHLGKLVWCT-R2 (SEQ ID NO: 64)

R1-CAWHQGKLVWCT-R2 (SEQ ID NO: 65)

R1-CAYHLGKLVWCT-R2 (SEQ ID NO: 66)

R1-CSWHLGKLVWCT-R2 (SEQ ID NO: 67)

R1-CAYHQGKLVWCT-R2 (SEQ ID NO: 68)

R1-CSWHQGKLVWCT-R2 (SEQ ID NO: 69)

R1-CSYHLGKLVWCT-R2 (SEQ ID NO: 70)

R1-CSYHQGKLVWCT-R2 (SEQ ID NO: 71)

R1-DCAWHLGKLVWC-R2 (SEQ ID NO: 72)

R1-DCAWHQGKLVWC-R2 (SEQ ID NO: 73)

R1-DCAYHLGKLVWC-R2 (SEQ ID NO: 74)

R1-DCSWHLGKLVWC-R2 (SEQ ID NO: 75)

R1-DCAYHQGKLVWC-R2 (SEQ ID NO: 76)

R1-DCSWHQGKLVWC-R2 (SEQ ID NO: 77)

R1-DCSYHLGKLVWC-R2 (SEQ ID NO: 78)

R1-DCSYHQGKLVWC-R2 (SEQ ID NO: 79)

R1-CAWHLGKLVWC-R2 (SEQ ID NO: 80)

R1-CAWHQGKLVWC-R2 (SEQ ID NO: 81)

R1-CAYHLGKLVWC-R2 (SEQ ID NO: 82)

R1-CSWHLGKLVWC-R2 (SEQ ID NO: 83)

R1-CAYHQGKLVWC-R2 (SEQ ID NO: 84)

R1-CSWHQGKLVWC-R2 (SEQ ID NO: 85)

R1-CSYHLGKLVWC-R2 (SEQ ID NO: 86)

R1-CSYHQGKLVWC-R2 (SEQ ID NO: 87)

wherein

R1=acetyl- and

R2=—COOH, -amide, the cysteines in positions X02 and X12 are optionally used for ring closure through disulfide bridging;

or the cysteines in positions X02 and X12 are replaced by Dpr or Dab or K or Orn for X02 in combination with D or E for X12 and employed for amide cyclization through the side chains;

or the cysteines in positions X02 and X12 are replaced by D or E for X02 in combination with Dpr or Dab or K or Orn for X12 and employed for amide cyclization through the side chains.

The mentioned peptides according to the invention bind immunoglobulins or antigen-immunoglobulin complexes in biological fluids.

Also claimed according to the invention are solid phases for affinity chromatography or solid-phase extraction consisting of organic, inorganic, synthetic polymers or of mixed polymers, preferably cross-linked agarose, cellulose, silica gel, polyamide and polyvinyl alcohols, which are optionally chemically activated, with peptides according to the invention immobilized on the surface of the solid phase.

In the solid phases according to the invention, the peptides are bound to the solid support phase preferably covalently or by adsorption. In another preferred embodiment of the solid phases according to the invention, the peptides are distanced from the support surface by linkers/spacers.

For coupling the peptides according to the invention to solid phases, they are preferably provided with a linker/spacer. Preferably, the linker/spacer is selected from the group consisting of:

Carboxylic acids and their derivatives, hydroxycarboxylic acids and their derivatives, oligoalkoxy derivatives and their oligomers, α-aminocarboxylic acids and their homo- and heterooligomers, α,ω-aminocarboxylic acids and their branched homo- and heterooligomers, other amino acids and their linear and branched homo- and heterooligomers, amino-oligoalkoxy-alkylamines and their linear and branched homo- and heterooligomers, maleinimidocarboxylic acid and its derivatives, oligomers of alkylamines, 4-alkylphenyl derivatives, 4-oligoalkoxyphenyl and 4-oligoalkoxyphenoxy derivatives, oligoalkylmercaptophenyl and 4-oligoalkylmercaptophenoxy derivatives, 4-oligoalkylaminophenyl and 4-oligoalkylaminophenoxy derivatives, (oligoalkylbenzyl)phenyl and 4-(oligoalkylbenzyl)phenoxy derivatives, and 4-(oligoalkoxybenzyl)phenyl and 4-(oligoalkoxybenzyl)phenoxy derivatives, trityl derivatives, benzyloxyaryl and benzyl-oxyalkyl derivatives, xanthen-3-yloxyalkyl derivatives, ω-(4-alkylphenyl) and ω-(4-alkylphenoxy)alkanoic acid derivatives, oligoalkylphenoxyalkyl and oligoalkoxyphenoxyalkyl derivatives, carbamate derivatives, amines, trialkylsilyl and dialkylalkoxysilyl derivatives, alkyl and aryl derivatives, thiols and their derivatives, thioethers and their derivatives, thiocarboxylic acids and their derivatives, thiolcarboxylic acids and their derivatives, sulfonic acids and their derivatives as well as combinations of the mentioned linkers or spacers.

The invention relates to a method for the adsorption of immunoglobulins to a solid phase, wherein the peptides according to the invention are bound to a solid phase usual in affinity chromatography or to mobile solid phases, and the immunoglobulin-containing samples to be adsorbed are contacted, in particular, with the solid phases according to the invention.

Preferably, a method for the adsorption of immunoglobulins is performed on a solid phase, wherein the peptides according to the invention are bound to a solid phase usual in affinity chromatography or to mobile solid phases, and the immunoglobulin-containing samples to be adsorbed are anticoagulant-treated human blood plasma or human whole blood and are contacted with the solid phases according to the invention.

The method according to the invention is suitable, in particular, for the adsorption of immunoglobulins from immunoglobulin-containing samples which contain auto-antibodies related to autoimmune diseases, especially rheumatoid diseases, multiple sclerosis, myasthenia gravis and other auto-antibody-mediated diseases.

The method according to the invention is advantageously performed with a device according to the invention for removing immunoglobulins from immunoglobulin-containing samples on solid phases, wherein the device contains a solid phase according to the invention, and means for the entry of immunoglobulin-containing samples are provided.

The invention also relates to the use of the peptides according to the invention, the solid phases according to the invention and the devices according to the invention for removing immunoglobulins from immunoglobulin-containing samples.

The invention is further illustrated by means of the following Examples.

EXAMPLE 1

Peptide Immobilization on Cellulose Matrix and Test for Immunoglobulin Binding

1. Synthesis of 13-mer Peptide Variants on a Support

Peptides consisting of 13 amino acids were synthesized by solid phase synthesis (Houghten, 1985) on a cellulose matrix with (βA)(βA) as a spacer group.

Starting from

```
R1-X01-X02-X03-X04-X05-X06-X07-X08-X09-X10-X11-
 - D - C - A - W - H - L - G - E - L - V - W -

X12-X13-R2
                                       C - T -
```

R1=amino

R2=(βA)(βA), where βA=β-alanine, peptide variants immobilized on solid phases were synthesized as described in Table 1.

2. Testing of the 13-mer Peptide Variants for Immunoglobulin Binding

The immobilized peptides were tested for their immunoglobulin binding capability by incubation with human IgG-Fc in a buffered solution and by incubation with human plasma.

Thus, the peptide variants immobilized on solid phases were washed with T-TBS buffer (136 mM NaCl, 1.6 mM KCl, 0.05% (v/v) Tween 20, 50 mM Tris-HCl, pH 8.0) and subsequently treated with blocking buffers (5% (w/v) saccharose, 4% (w/v) bovine serum albumin in T-TBS). Incubation of the immobilized peptides with IgG-Fc (1 µg/ml) in blocking buffer and human serum (diluted 1:10,000 in blocking buffer) was effected for 3 h at room temperature. For checking the specificity of the binding, buffered serum albumin solution (blocking buffer) without addition was included as a control. Thereafter, the peptide variants immobilized on the solid phases were washed three more times with T-TBS buffer.

After incubation with alkaline phosphatase-conjugated anti-human IgG antibody (1.2 µg/ml) in blocking buffer, detection of the immunoglobulin binding was effected by means of NBT (nitroblue tetrazolium chloride)/BCIP (5-bromo-4-chloro-3-indolyl phosphate toluidine salt) as a substrate (200 µl of parent solution (18.75 mg/ml NBT and 9.4 mg/ml BCIP in 67% (v/v) DMSO) in 10 ml developing buffer (100 mM Tris-HCl, 100 mM NaCl, 5 mM MgCl$_2$, pH 9.5)).

The results of the tests for immunoglobulin binding are represented in Table 1.

EXAMPLE 2

Peptides Immobilized on Agarose Beads with Glu (E) as Compared to Lys (K) in Peptide Position X08 (See Above) and Test of Immunoglobulin Binding from Human Plasma

1. Immobilization

For immobilization to a solid phase, the peptides were dissolved in coupling buffer (30% (v/v) acetonitrile, 0.5 M NaCl, 0.1 M NaHCO$_3$, pH 8.3) to a concentration of 1 mg/ml and mixed with washed and CNBr-preactivated sepharose 4B at a volume ratio of 10:1. After completion of the coupling reaction, the peptide. matrices were washed with coupling buffer, and the excess CNBr groups were inactivated by incubation of the matrix in Tris buffer (100 mM Tris-HCl, 500 mM NaCl, pH 8.0).

The peptide loadings of the matrices were determined by photometry (A$_{280\ nm}$) by establishing the difference between the peptide mass employed before coupling and the non-immobilized peptide mass after coupling.

The results of the peptide loadings are represented in Table 2.

Immobilized peptides:

linear peptides
(SEQ ID NO:90)
acetyl-D-S-A-W-H-L-G-E-L-V-W-C-T-((βA)(βA)K)

peptides cyclized through disulfide bridging
acetyl-D-C-A-E-H-L-G-E-L-V-W-C-T-((βA)(βA)K)

acetyl---C-A-W-H-Q-G-E-L-V-W-C---((βA)GKK)

acetyl-D-C-A-W-H-L-G-K-L-V-W-C-T-amide peptides cyclized through side-chain amide bonding
acetyl-D-D-A-W-H-L-G-E-L-V-W-(Dpr)-T-((βA)(βA)K)

acetyl-D-(Dpr)-A-W-H-L-G-E-L-V-W-D-T-((βA)(βA)K)

Dpr = diaminopropionic acid

Dpr=diaminopropionic

2. Immunoglobulin Binding from Human Plasma

The peptide matrices were tested by means of affinity chromatography for their binding capacity and binding specificity for immunoglobulins with human plasma as a sample. Thus, 6 volume fractions of human plasma as the sample was passed through 1 column volume fraction of peptide matrix at a linear flow rate of 80 cm/h.

Prior to sample application, the affinity-chromatographic column was equilibrated with PBS, pH 7.2. After sample application, the column was washed with PBS, pH 7.2, until the adsorption baseline was reached, followed by eluting the bound protein with 30 mM Na citrate buffer, pH 2.8.

The determination of the concentration of the eluted protein was effected by photometric measurement of the adsorption at 280 nm. The immunoglobulin concentration was calculated therefrom with $\epsilon_{280\ nm}$=1.35 cm$^2$/mg for IgG.

The results of the capacity determinations are represented in Table 2.

The specificity of the immunoglobulin-peptide bonding was determined by means of SDS-PAGE. It was compared with the specificity for immunoglobulin of protein A and anti-IgG antibodies.

Thus, the eluates of the respective affinity chromatography run (as described above) were processed for SDS-PAGE under reducing conditions.

The results of the specificity testing are represented in FIG. 1.

EXAMPLE 3

Glu (E) as Compared to Lys (K) in Peptide Position X08 (See Above): Peptide Immobilization on Agarose Beads and Test of Immunoglobulin Binding from Human Plasma before and after Thermal Treatment

1. Immobilization

For immobilization to a solid phase, the peptides were dissolved in coupling buffer (30% (v/v) acetonitrile, 0.5 M NaCl, 0.1 M NaHCO$_3$, pH 8.3) to a concentration of 1 mg/ml and mixed with washed and CNBr-preactivated sepharose 4B at a volume ratio of 10:1. After completion of the coupling reaction, the peptide matrices were washed with coupling buffer, and the excess CNBr groups were inactivated by incubation of the matrix in Tris buffer (100 mM Tris-HCl, 500 mM NaCl, pH 8.0).

The peptide loadings of the matrices were determined by photometry (A$_{280\ nm}$) by establishing the difference between the peptide mass employed before coupling and the non-immobilized peptide mass after coupling.

Immobilized Peptides

All the mentioned peptides are cyclized through disulfide bridging.

MF0147

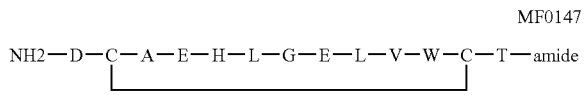

Immobilization through the amino terminus.

MF0146

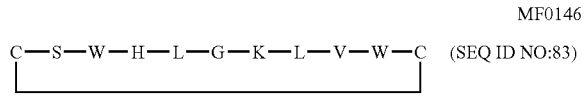 (SEQ ID NO:83)

Immobilization through the ε-amino group of lysine (K)

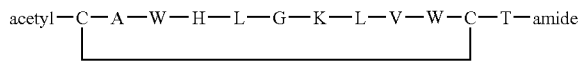

Immobilization through the ε-amino group of lysine (K)

2. Immunoglobulin Binding from Human Plasma before and after Autoclavation of the Peptide Matrices Before and after autoclavation at 121° C. for 20 min, the peptide matrices were tested by means of affinity chromatography for their binding capacity and binding specificity for immunoglobulins with human plasma as a sample. Thus, 6 volume fractions of human plasma as the sample was passed through 1 column volume fraction of peptide matrix at a linear flow rate of 80 cm/h.

Prior to sample application, the affinity-chromatographic column was equilibrated with PBS, pH 7.2. After sample application, the column was washed with PBS, pH 7.2, until the adsorption baseline was reached, followed by eluting the bound protein with 30 mM Na citrate buffer, pH 2.8.

The determination of the concentration of the eluted protein was effected by photometric measurement of the adsorption at 280 nm. The immunoglobulin concentration was calculated therefrom with $\epsilon_{280\ nm}=1.35\ cm^2/mg$ for IgG.

The results of the capacity determinations are represented in Table 3.

The specificity of the immunoglobulin-peptide bonding was determined by means of SDS-PAGE before and after autoclavation.

Thus, the eluates of the respective affinity chromatography run (as described above) were processed for SDS-PAGE under reducing conditions.

Figure 2:
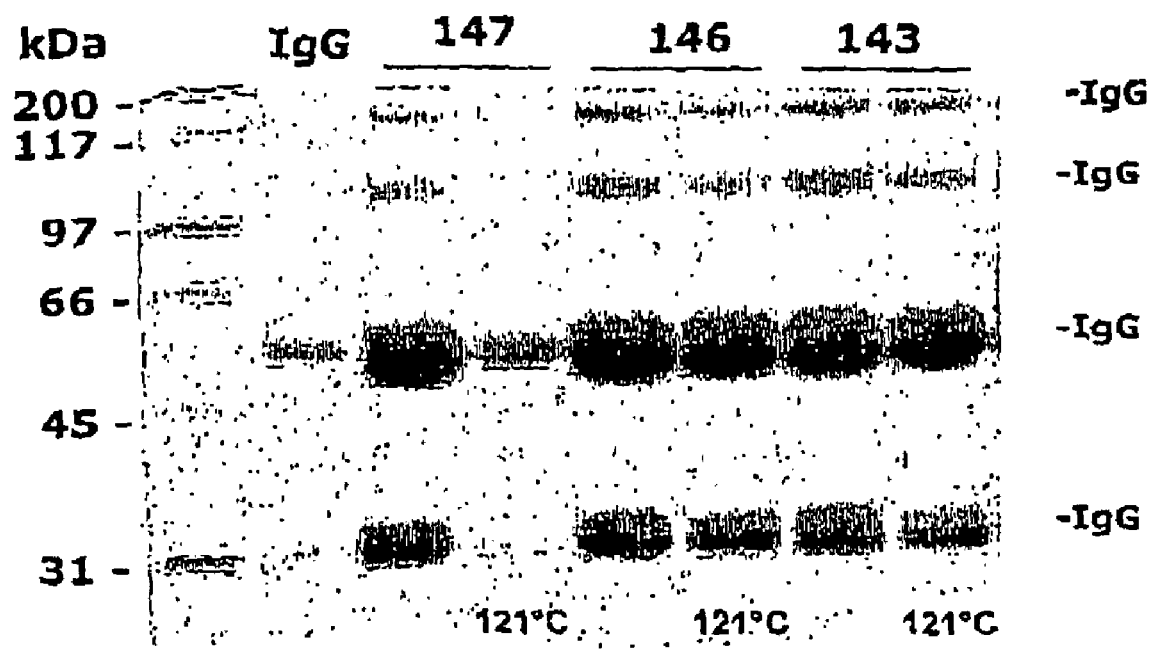

The results of the specificity testing are represented in FIG. 2.

TABLE 1

Testing of 248 peptide variants (13-mers) for immunoglobulin binding

| | A | C | D | E | F | G | H | I | K | L | M | N | P | Q | R | S | T | V | W | Y |
|---|---|---|---|---|---|---|---|---|---|---|---|---|---|---|---|---|---|---|---|---|
| (A) Result for incubation with serum albumin: | | | | | | | | | | | | | | | | | | | | |
| 01 | 0 | 0 | 0 | 0 | 0 | 0 | 0 | 0 | 0 | 0 | 0 | 0 | 0 | 0 | 0 | 0 | 0 | 0 | 0 | 0 |
| 02 | 0 | 0 | 0 | 0 | 0 | 0 | 0 | 0 | 0 | 0 | 0 | 0 | 0 | 0 | 0 | 0 | 0 | 0 | 0 | 0 |
| 03 | 0 | 0 | 0 | 0 | 0 | 0 | 0 | 0 | 0 | 0 | 0 | 0 | 0 | 0 | 0 | 0 | 0 | 0 | 0 | 0 |
| 04 | 0 | 0 | 0 | 0 | 0 | 0 | 0 | 0 | 0 | 0 | 0 | 0 | 0 | 0 | 0 | 0 | 0 | 0 | 0 | 0 |
| 05 | 0 | 0 | 0 | 0 | 0 | 0 | 0 | 0 | 0 | 0 | 0 | 0 | 0 | 0 | 0 | 0 | 0 | 0 | 0 | 0 |
| 06 | 0 | 0 | 0 | 0 | 0 | 0 | 0 | 0 | 0 | 0 | 0 | 0 | 0 | 0 | 0 | 0 | 0 | 0 | 0 | 0 |
| 07 | 0 | 0 | 0 | 0 | 0 | 0 | 0 | 0 | 0 | 0 | 0 | 0 | 0 | 0 | 0 | 0 | 0 | 0 | 0 | 0 |
| 08 | 0 | 0 | 0 | 0 | 0 | 0 | 0 | 0 | 0 | 0 | 0 | 0 | 0 | 0 | 0 | 0 | 0 | 0 | 0 | 0 |
| 09 | 0 | 0 | 0 | 0 | 0 | 0 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 | 0 | 0 | 0 | 0 | 0 | 0 | 0 |
| (B) Result for incubation with human plasma: | | | | | | | | | | | | | | | | | | | | |
| 01 | + | 0 | + | + | 0 | + | 0 | 0 | 0 | 0 | 0 | 0 | 0 | 0 | 0 | 0 | 0 | 0 | 0 | 0 |
| 02 | 0 | + | 0 | 0 | 0 | 0 | 0 | 0 | 0 | 0 | 0 | 0 | 0 | 0 | 0 | 0 | 0 | 0 | 0 | 0 |
| 03 | + | 0 | 0 | 0 | 0 | 0 | 0 | 0 | 0 | 0 | 0 | 0 | 0 | 0 | + | + | 0 | 0 | 0 | 0 |
| 04 | 0 | 0 | 0 | + | + | 0 | + | 0 | + | 0 | + | 0 | 0 | 0 | + | + | + | + | + | + |
| 05 | 0 | 0 | 0 | 0 | 0 | 0 | + | 0 | 0 | 0 | 0 | 0 | 0 | 0 | 0 | 0 | 0 | 0 | 0 | 0 |
| 06 | 0 | 0 | 0 | 0 | 0 | + | + | 0 | + | + | + | + | 0 | + | + | 0 | 0 | 0 | 0 | 0 |
| 07 | 0 | 0 | + | 0 | 0 | + | 0 | 0 | 0 | 0 | 0 | 0 | 0 | 0 | 0 | 0 | 0 | 0 | 0 | 0 |
| 08 | 0 | 0 | + | + | 0 | 0 | + | 0 | + | 0 | + | + | 0 | + | + | 0 | 0 | 0 | 0 | 0 |
| 09 | 0 | 0 | 0 | 0 | 0 | 0 | 0 | 0 | + | + | 0 | 0 | 0 | 0 | + | 0 | 0 | 0 | 0 | 0 |
| 10 | 0 | 0 | 0 | 0 | 0 | 0 | 0 | 0 | 0 | 0 | 0 | 0 | 0 | 0 | 0 | 0 | 0 | + | 0 | 0 |
| 11 | 0 | 0 | 0 | 0 | 0 | 0 | 0 | 0 | 0 | 0 | 0 | 0 | 0 | 0 | 0 | 0 | 0 | 0 | + | 0 |
| 12 | 0 | + | 0 | 0 | 0 | 0 | 0 | 0 | 0 | 0 | 0 | 0 | 0 | 0 | 0 | 0 | 0 | 0 | 0 | 0 |
| 13 | 0 | 0 | + | + | 0 | 0 | 0 | 0 | + | 0 | 0 | 0 | 0 | 0 | + | + | + | 0 | 0 | 0 |
| (C) Result for incubation with human IgG-Fc: | | | | | | | | | | | | | | | | | | | | |
| 01 | + | 0 | + | + | 0 | + | + | 0 | + | + | + | + | + | + | + | 0 | 0 | 0 | 0 | 0 |
| 02 | 0 | + | 0 | 0 | 0 | 0 | 0 | 0 | 0 | 0 | 0 | 0 | 0 | 0 | 0 | 0 | 0 | 0 | 0 | 0 |
| 03 | + | 0 | 0 | + | 0 | 0 | 0 | 0 | + | 0 | 0 | 0 | 0 | + | 0 | + | + | 0 | 0 | 0 |
| 04 | 0 | 0 | 0 | 0 | + | + | 0 | + | + | + | + | + | 0 | + | + | + | + | + | + | + |

TABLE 1-continued

Testing of 248 peptide variants (13-mers) for immunoglobulin binding

|    | A | C | D | E | F | G | H | I | K | L | M | N | P | Q | R | S | T | V | W | Y |
|----|---|---|---|---|---|---|---|---|---|---|---|---|---|---|---|---|---|---|---|---|
| 05 | 0 | 0 | 0 | 0 | 0 | 0 | + | 0 | 0 | 0 | 0 | 0 | 0 | 0 | 0 | 0 | 0 | 0 | 0 | 0 |
| 06 | + | 0 | + | + | 0 | + | + | 0 | + | + | + | + | 0 | + | + | + | + | 0 | 0 | 0 |
| 07 | 0 | 0 | + | 0 | 0 | + | 0 | 0 | 0 | 0 | 0 | 0 | 0 | 0 | 0 | 0 | 0 | 0 | 0 | 0 |
| 08 | + | 0 | + | + | 0 | 0 | + | 0 | + | 0 | + | 0 | + | + | + | + | 0 | 0 | 0 | 0 |
| 09 | 0 | 0 | 0 | 0 | 0 | 0 | 0 | 0 | + | + | + | 0 | + | + | + | 0 | 0 | 0 | 0 | 0 |
| 10 | 0 | 0 | 0 | 0 | 0 | 0 | 0 | 0 | 0 | 0 | 0 | 0 | 0 | 0 | 0 | 0 | + | 0 | 0 | 0 |
| 11 | 0 | 0 | 0 | 0 | 0 | 0 | + | 0 | + | 0 | 0 | 0 | 0 | 0 | 0 | 0 | 0 | + | 0 |
| 12 | 0 | + | 0 | 0 | 0 | 0 | 0 | 0 | 0 | 0 | 0 | 0 | 0 | 0 | 0 | 0 | 0 | 0 | 0 | 0 |
| 13 | + | 0 | + | + | 0 | 0 | + | 0 | + | 0 | + | 0 | + | + | + | + | 0 | 0 | 0 |

(A) Incubation of the peptide variants immobilized to the solid phase with serum albumin as a negative control
(B) Incubation of the peptide variants immobilized to the solid phase with human plasma as a sample
(C) Incubation of the peptide variants immobilized to the solid phase with human IgG-Fc as a sample
The detection of the binding of immunoglobulins to the peptide variants immobilized to the solid phase was effected by means of alkaline phosphatase-conjugated anti-human IgG antibody.
First row: one-letter code for the exchanged amino acid
First column: sequence position of the exchanged amino acid
No binding of immunoglobulin for the defined peptide variant, detection negative: 0
Binding of immunoglobulin for the defined peptide variant, detection positive: +

TABLE 2

Binding capacity of the peptide matrices for immunoglobulins

| Peptide matrix | Loading | Volume capacity | Rel. capacity |
|---|---|---|---|
| A1 | 8.8 | 4.70 | 0.53 |
| B1 | 8.2 | 1.18 | 0.14 |
| B2 | 8.5 | 5.87 | 0.69 |
| B3 | 7.7 | 10.7 | 1.40 |
| C1 | 8.0 | 1.74 | 0.22 |
| C2 | 8.8 | 1.50 | 0.17 |

Loading: mg of immobilized peptide/ml of matrix [mg/m/].
Volume capacity: mg of bound protein/ml of peptide matrix [mg/ml].
Relative capacity: mg of bound protein/mg of peptide matrix loading [mg/mg].

FIG. 1: Specificity of immunoglobulin-peptide binding

The specificity of the immunoglobulin-peptide binding (A) in SDS-PAGE was compared with the specificity of the immunoglobulin-protein A binding (Prot. A) and with the specificity of the binding of human IgG with a chicken IgY anti-human IgG antibody (AK1) and a sheep IgG anti-human IgG antibody (AK2) (B) as well as with the specificity of the immunoglobulin-peptide RTY binding, (acetyl-(RTY)βA))$_2$KGKK-amide derived from Fassina et al. (1996) and the specificity of the immunoglobulin-peptide K1- and K2 binding, wherein K1 is acetyl-FGRLVSSIRY(βA)(γA)K-amide and K2 is acetyl-TWKTSRISIF(βA)(βA)K-amide, derived from Krook et al. (1998) (C).

(A)
Markers: markers for molecular mass, in kDa.
HP: human plasma sample, 10 μl sample, prediluted in PBS 1:200.
IgG: human immunoglobulin G, 1.25 μg.

Linear Peptides
A1: eluate from peptide matrix A1, 10 μl sample

Peptides cyclized through disulfide bridging
B1: eluate from peptide matrix B1, 10 μl sample
B2: eluate from peptide matrix B2, 10 μl sample
B3: eluate from peptide matrix B3, 10 μl sample Peptides cyclized through side-chain amide bonding
C1: eluate from peptide matrix C1, 10 μl sample
C2: eluate from peptide matrix C2, 10 μl sample (B)
Ak1: eluate from antibody matrix 1, 10 μl sample
Ak2: eluate from antibody matrix 2, 10 μl sample
Prot. A: eluate from protein A matrix, 10 μl sample (C)
RTY: eluate from peptide matrix RTY, 10 μl sample
K1: eluate from peptide matrix K1, 10 μl sample
K2: eluate from peptide matrix K2, 10 μl sample The SDS-PAGE sample preparation was effected under reducing conditions.

TABLE 3

Binding capacity of the peptide matrices for immunoglobulins before and after autoclavation

| Peptide matrix | Rel. capacity before autoclavation | [%] | Rel. capacity after autoclavation | [%] | Relative residual capacity, based on MF147 |
|---|---|---|---|---|---|
| MF0147 | 5.11 | 100 | 0.72 | 14 | 100% |
| MF0146 | 3.48 | 100 | 1.88 | 54 | 386% |
| MF0143 | 2.85 | 100 | 1.85 | 65 | 464% |

Relative capacity: mg of bound protein/mg of peptide matrix loading [mg/mg].

FIG. 2: Specificity of immunoglobulin-peptide binding before and after auto-clavation
Markers: markers for molecular mass, in kDa.
IgG: human immunoglobulin G, 1.25 μg.
147, 146, 143: eluates of the respective peptide matrix before autoclavation, 10 μl sample each
121° C.: eluate after autoclavation of the matrix at 121° C. for 20 min, 10 μl sample each
The SDS-PAGE sample preparation was effected under reducing conditions.

REFERENCES

Davies D R, Metzger H. Structural basis of antibody function. Annu Rev Immunol 1983;1:87–117

Alt F W, Blackwell T K, Yancopoulos G D Development of the primary antibody repertoire. Science Nov. 20, 1987; 238(4830):1079–87

McKenzie S E, Schreiber A D. Biological advances and clinical applications of Fc receptors for IgG. Curr Opin Hematol January 1994;1(1):45–52

Makiya R, Stigbrand T., Placental alkaline phosphatase as the placental IgG receptor. Clin Chem December 1992; 38(12):2543–5

Sarfati M, Fournier S, Wu C Y, Delespesse G., Expression, regulation and function of human Fc epsilon RII (CD23) antigen. Immunol Res. 1992;11(3–4):260–72

Capron M, Truong M J, Aldebert D, Gruart V, Suemura M, Delespesse G, Tourvieille B, Capron A., Eosinophil IgE receptor and CD23 Immunol Res. 1992;11(3–4): 252–9

Shen L, Receptors for IgA on phagocytic cells Immunol Res. 1992;11(3–4):273–82. Review.

Sandor M, Ibraghimov A, Rosenberg M G, Teeraratkul P, Lynch R G, Expression of IgA and IgM Fc receptors on murine T lymphocytes. Immunol Res. 1992;11(3–4): 169-80.

Miletic V D, Frank M M, Complement-immunoglobulin interactions. Curr Opin Immunol. February 1995;7(1): 41–7

Stahl S, Nygren P A, Sjolander A, Uhlen M, Engineered bacterial receptors in immunology. Curr Opin Immunol. April1993;5 (2):272–7

Belak M, Borberg H, Jimenez C, Oette K, Technical and clinical experience with protein A immunoadsorption columns. Transfus Sci December1994;15(4):419–22

Samuelsson G, Immunoadsorption using the Excorim treatment system. Transfus Sci March1998;19 Suppl:3–4

Felson D T, LaValley M P, Baldassare A R, Block J A, Caldwell J R, Cannon G W, Deal C, Evans S, Fleischmann R, Gendreau R M, Harris E R, Matteson E L, Roth S H, Schumacher H R, Weisman M H, Furst D E, The Prosorba column for treatment of refractory rheumatoid arthritis: a randomized, double-blind, sham-controlled trial. Arthritis Rheum October 1999;42(10):2153–9

Koll RA, Ig-Therasorb immunoadsorption for selective removal of human immunoglobulins in diseases associated with pathogenic antibodies of all classes and IgG subclasses, immune complexes, and fragments of immunoglobulins. Ther Apher May 1998;2(2):147–52

Knobl P, Derfler K, Extracorporeal immunoadsorption for the treatment of haemophilic patients with inhibitors to factor VIII or IX. Vox Sang 1999;77 Suppl 1:57–64

Jimenez C, Rosenow F, Grieb P, Haupt W F, Borberg H, Adsorption therapy with tryptophan-conjugated polyvinyl alcohol gels in 10 patients with acute Guillain-Barre syndrome. Transfus Sci January 1993;14(1):9–11

Fadul J E, Danielson B G, Wikstrom B, Reduction of plasma fibrinogen, immunoglobulin G, and immunoglobulin M concentrations by immunoadsorption therapy with tryptophan and phenylalanine adsorbents. Artif Organs September 1996;20(9) :986–90

Takamori M, Ide Y, Specific removal of anti-acetylcholine receptor antibodies in patients with myasthenia gravis. Transfus Sci September 1996;17(3):445–53

Fassina G, Verdoliva A, Odierna M R, Ruvo M, Cassini G, Protein A mimetic peptide ligand for affinity purification of antibodies. J Mol Recognit September-December 1996;9(5–6):564–9

Fassina G, Verdoliva A, Palombo G, Ruvo M, Cassani G, Immunoglobulin specificity of TG19318: a novel synthetic ligand for antibody affinity purification. J Mol Recognit 1998 Winter;11(1–6):128–33

DeLano W L, Ultsch M H, de Vos A M, Wells J A, Convergent solutions to binding at a protein-protein interface. Science Feb. 18, 2000;287(5456):1279–83

Krook M, Mosbach K, Ramstrom O, Novel peptides binding to the Fc-portion of immunoglobulins obtained from a combinatorial phage display peptide library. J Immunol Methods Dec. 1, 1998;221(1–2):151–7

Houghten R A, General method for the rapid solid-phase synthesis of large numbers of peptides: specificity of antigen-antibody interaction at the level of individual amino acids. Proc Natl Acad Sci USA 1985 Aug;82(15): 5131–5.

---

The invention claimed is:

1. A peptide having amino acid sequence $R^1$ X01 X02 X03 X04 H X06 X07 X08 X09 X10 X11 X12 X13 $R^2$ (SEQ ID NO: 91), wherein,
- $R^1$=amino, acetyl, or deletion,
- X01=A, D, E, G, or deletion,
- X02=C, D, E, diaininobutyric acid (Dab), diaminopropionic acid (Dpr), K, or ornithine (Orn),
- X03=A, S, or T,
- X04=E, F, H, R, S, T, V, W, or Y,
- X06=E, G, H, L, N, Q, or R,
- X07=K, D or G,
- X08=K,
- X09=L,
- X10=V,
- X11=W,
- X12=C, S, D, E, diaminobutryic acid (Dab), diaminopropionic acid (Dpr), K, or ornithine (Orm),
- X13=D, E, K, Q, R, S, T, or deletion, and
- $R^2$=COOH, amide, GK, GKK, (βA)GK, (βA)GKK, (SEQ ID NO: 89), (βA)(βA), (βA)(βA)K, or deletion, wherein deletion is represented by (−).

2. The peptide according to claim 1 in a cyclic form, peptide ring closure being effected
   a) through disulfide bridging between C=X02 and C=X12,
   b) through amide cyclization between X02 and X12, or
   c) through a combination of the disulfide bridging and the amide cyclization.

3. The peptide according to claim 1 wherein the amino acid sequence is $R^1$ ACAWHLGKLVWCT $R^2$ (SEQ ID NO: 1), $R^1$ ECAWHLGKLVWCT $R^2$ (SEQ ID NO: 2), $R^1$ GCAWHLGKLVWCT $R^2$ (SEQ ID NO: 3), $R^1$-CAWHLGKLVWCT $R^2$ (SEQ ID NO: 4), $R^1$ DCSWHLGKLVWCT $R^2$ (SEQ ID NO: 6), $R^1$ DCTWHLGKLVWCT $R^2$ (SEQ ID NO: 7), $R^1$ DCAEHLGKLVWCT $R^2$ (SEQ ID NO: 8), $R^1$ DCAYHLGKLVWCT $R^2$ (SEQ ID NO: 9), $R^1$ DCAHHLGKLVWCT $R^2$ (SEQ ID NO: 10), $R^1$ DCARHLGKLVWCT $R^2$ (SEQ ID NO: 13), $R^1$ DCASHLGKLVWCT $R^2$ (SEQ ID NO: 14), $R^1$ DCATHLGKLVWCT $R^2$ (SEQ ID NO: 15), $R^1$ DCAVHLGKLVWCT $R^2$ (SEQ ID NO: 16), $R^1$ DCAWHLGKLVWCT $R^2$ (SEQ ID NO: 17), $R^1$ DCAYHLGKLVWCT $R^2$ (SEQ ID NO: 18), $R^1$ DCAWHEGKLVWCT $R^2$ (SEQ ID NO: 20), $R^1$ DCAWHGGKLVWCT $R^2$ (SEQ ID NO: 21), $R^1$ DCAWHHGKLVWCT $R^2$ (SEQ ID NO: 22),

R¹ DCAWHNGKLVWCT R² (SEQ ID NO: 23),

R¹ DCAWHQGKLVWCT R² (SEQ ID NO: 26),

R¹ DCAWHRGKLVWCT R² (SEQ ID NO: 27),

R¹ DCAWHLDKLVWCT R² (SEQ ID NO: 28),

R¹ DCAWHLGKLVWCD R² (SEQ ID NO: 39),

R¹ DCAWHLGKLVWCE R² (SEQ ID NO: 40),

R¹ DCAWHLGKLVWCK R² (SEQ ID NO: 41),

R¹ DCAWHLGKLVWCQ R² (SEQ ID NO: 42),

R¹ DCAWHLGKLVWCR R² (SEQ ID NO: 43),

R¹ DCAWHLGKLVWCS R² (SEQ ID NO: 44),

R¹ DCAWHLGKLVWC R² (SEQ ID NO: 45), wherein
  R¹=amino or acetyl and
  R²=COOH, amide, GK, GKK, (βA)GK, (βA)GKK (SEQ ID NO: 89), (βA)(βA), or (βA)(βA)K.

4. The peptide according to claim 1:
a) wherein
  X01=A, E, G or deletion,
  X02=C,
  X03=S or T,
  X04=E, F, H, R, S, T, V, or Y,
  X06=G, H, N, Q, or R,
  X07=D,
  X08=K,
  X09=L,
  X10=V,
  X11=W,
  X12=C, and
  X13 D, E, K, Q, R, S, or deletion;
b) wherein
  X01=A, E, G, or deletion,
  X02=C
  X03=S or T,
  X04=E, F, H, R, S, T, V, or Y,
  X06=G, H, N, Q, or R,
  X07=D,
  X13=D, E, K, Q, R, S, or deletion;
c) wherein
  X01=A, E, G, or deletion,
  X02=C,
  X03=S or T,
  X04=V, W, or Y,
  X06=G, H, N, Q, or R,
  X07=D,
  X08=K,
  X09=L,
  X10=V,
  X11=W,
  X12=C, and
  X13=D, E, K, Q, K, S, or deletion;
d) wherein
  X01=A, E, G, or deletion,
  X02=C,
  X03=S or T,
  X04=E, F, H, R, S, T, V, or Y,
  X06=E, G, H, N, Q, or R,
  X07=D,
  X08=K,
  X09=L,
  X10=V,
  X11=W,
  X12=C, and
  X13D, E, K, Q, K, S, or deletion;
e) wherein
  X01=A, E, G, or deletion,
  X02=C,
  X03=S or T,
  X04=E, F, H, R, S, T, V, or Y,
  X06=G, H, N, Q, R,
  X07=D,
  X08=K,
  X09=L,
  X10=V,
  X11=W,
  X12=C, and
  X13=D, E, K, Q, R, S, or deletion;
or
f) wherein
  X01=A, E, G, or deletion,
  X02=C,
  X03=S or T,
  X04=E, F, H, K, M, R, S, T, V, or Y,
  X06=G, H, K, M, N, Q, or R,
  X07=D,
  X08=K,
  X09=L,
  X10=V,
  X11=W,
  X12=C, and
  X13=D, E, K, Q, R, S, or deletion;
wherein
  R¹=amino or acetyl and
  R²=COOH, amide, GK, GKK, (βA)GK, (βA)GKK (SEQ ID NO: 89), (βA)(βA), or (βA)(βA)K.

5. The peptide according to claim 1 in cyclic form, peptide ring formation being effected through:
  1) disulfide bridging, between X02 and X12, when C=X02 and C=X12,
  2) amide cyclization, between X02 and X12, when X02 is Dpr, Dab, K, or Orn in combination with D or E=X12,
  3) amide cyclization, between X02 and X12, when X02 is D or E in combination with Dpr, Dab, K, or Orn=X12,
  4) amide cyclization, when R¹=COOH and Dpr, Dab, K, or Orn=X02, between X02 and the peptide's C-terminal amino acid,
  5) amide cyclization, when R¹=NH₂ and E or D=X12, between X12 and the peptide's N-terminal amino acid, or
  6) amide cyclization, when R¹=NH₂ and R¹=COOH, between the N-terminal and C-terminal amino acids,
  a) wherein
    X01=A, E, G, or deletion,
    X02=C, D, E, diaminobutyric acid (Dab), diaminopropionic acid (Dpr), K, or ornithine (Orn),
    X03=A,
    X04=W,
    X06=L,
    X07=G,
    X08=K,
    X09=L,
    X10=V,
    X11=W,
    X12=C, and
    X13=T;

b) wherein
- X01=D,
- X02=C,
- X03=S or T,
- X04=W,
- X06=L,
- X07=G,
- X08=K,
- X09=L,
- X10=V,
- X11=W,
- X12=C, and
- X13=T;

c) wherein
- X01=D,
- X02=C, D, E, diaminobutryic acid (Dab), diaminopropionic acid (Dpr), K, or ornithine (Orn),
- X03=A,
- X04=E, F, H, R, S, T, V, W, or Y,
- X06=L,
- X07=G,
- X08=K,
- X09=L,
- X10=V,
- X11=W,
- X12=C, and
- X13=T;

d) wherein
- X01=D,
- X02=C, D, E, diaminobutyric acid (Dab), diaminopropionic acid (Dpr), K, or ornithine (Orn),
- X03=A,
- X04=W,
- X06=E, G, H, N, Q, R,
- X07=G,
- X08=K,
- X09=L,
- X10=V,
- X11=W,
- X12=C, and
- X13=T;

e) wherein
- X01=D,
- X02=C, D, E, diminobutyric acid (Dab), diaminopropionic acid (Dpr), K, or ornithine (Orn),
- X03=A,
- X04=W,
- X06=L,
- X07=D,
- X08=K,
- X09=L,
- X10=V,
- X11=W
- X12=C, and
- X13=T;

f) wherein
- X01=D,
- X02=C, D, E, diaminobutyric acid (Dab), diaminopropionic acid (Dpr), K, or ornithine (Orn),
- X03=A,
- X04=W,
- X06=L,
- X07=G,
- X08=K,
- X09=L,
- X10=V,
- X11=W,
- X12=C, and
- X13=D, E, K, Q, R, S, or deletion;

g) wherein
- X01=D,
- X02=C, D, E, diaminobutyric acid (Dab), diaminopropionic acid (Dpr), K, or ornithine (Orn),
- X03=A,
- X04=W,
- X06=L,
- X07=D,
- X08=K,
- X09=L,
- X10=V,
- X11=W,
- X12=C, and
- X13=T;

h) wherein
- X01=D,
- X02=C, D, E, diaminobutyric acid (Dab), diaminopropionic acid (Dpr), K. or ornithine (Orn),
- X03=A,
- X04=W,
- X06=L,
- X07=K,
- X08=K,
- X09=L,
- X10=V,
- X11=W,
- X12=C, and
- X13=T;

i) wherein
- X01=D,
- X02=C, D, E, diamninobutyric acid (Dab), diaminopropionic acid (Dpr), K, or ornithine (Orn),
- X03=A,
- X04=W,
- X06=L,
- X07=D,
- X08=K,
- X09=L,
- X10=V,
- X11=W,
- X12=C, and
- X13=T;

j) wherein
- X01=D,
- X02=C, D, E, diaminobutyric avid (Dab), diaminopropionic acid (Dpr), K, or ornithine (Orn),
- X03=A,
- X04=W,
- X06=L,
- X07=D,
- X08=K,
- X09=L,
- X10=V,
- X11=W,
- X12=C, and
- X13=T;

or k) wherein
- X01=D,
- X02=C, D, E, diaminobutyric acid (Dab), diaminopropionic acid (Dpr), K, or ornithine (Orn),
- X03=A,
- X04=W,
- X06=L,
- X07=D, X08=K,
X09=L,
X10=V,
X11=W,
X12=C, and
X13=T;
wherein
R$^1$=amino or acetyl and
R$^2$=COOH, amide, GK, GKK, (βA)GK, (βA)GKK (SEQ ID NO: 89), (βA)(βA), or (βA)(βA)K.

6. The peptide according to claim 1 in cyclic form, peptide ring formation being effected through:
1) disulfide bridging, between X02 and X12, when C=X02 and C=X12,
2) amide cyclization, between X02 and X12, when X02 is Dpr, Dab, K, or Orn in combination with D or E=X12,
3) amide cyclization, between X02 and X12, when X02 is D or E in combination with Dpr, Dab, K, or Orn=X12,
4) amide cyclization, when R$^2$=COOH and Dpr, Dab, K, or Orn=X02, between X02 and the peptide's C-terminal amino acid,
5) amide cyclization, when R$^1$=NH$_2$ and E or D=X12, between X12 and the peptide's N-terminal amino acid, or
6) cyclization, when R$^1$=NH$_2$ and R$^2$=COOH, between the N-terminal and C-terminal amino acids, a) wherein
X01=D,
X02=C, D, E, diamninobutyric acid (Dab), diaminopropionic acid (Dpr), K, or ornithine (Orn),
X03=S or T,
X04=E, F, H, R, S, T, V, or Y,
X06=G, H, N, Q, or R,
X07=D,
X08=K,
X09=L,
X10=V,
X11=W,
X12=C, and
X13=D, E, K, Q, R, S, or deletion;

b) wherein
X01=A, E, G, or deletion,
X02=C, D, E, diaminobutyric acid (Dab), diaminopropionic acid (Dpr), K, or ornithine (Orn),
X03=A,
X04=E, F, H, R, S, T, V, or Y,
X06=G, H, N, Q, or R,
X07=D,
X08=K,
X09=L,
X10=V,
X11=W,
X12=C, and
X13=D, E, K, Q, R, S, or deletion;

c) wherein
X01=A, E, G, or deletion,
X02=C, D, E, diaminobutyric acid (Dab), diaminopropionic acid (Dpr), K, or ornithine (Orn),
X03=S or T,
X04=W,
X06=G, H, N, Q, or R,
X07=D,
X08=K,
X09=L,
X10=V,
X11=W,
X12=C, and
X13=D, E, K, Q, R, S, or deletion;

d) wherein
X01=A, E, G, or deletion,
X02=C, D, E, diaminobutyric acid (Dab), diaminopropionic acid (Dpr), K, or ornithine (Orn),
X03=S or T,
X04=E, F, H, R, S, T, V, or Y,
X06=L,
X07=D,
X13=D, E, K, Q, R, S, or deletion;

e) wherein
X01=A, E, G, or deletion,
X02=C, D, E, diaminobutyric acid (Dab), diaminopropionic acid (Dpr), K, or ornithine (Orn),
X03=S or T,
X04=E, F, H, R, S, T, V, or Y,
X06=G, H, N, Q, or R,
X07=D,
X08=K,
X09=L,
X10=V,
X11=W,
X12=C, and
X13=D, E, K, Q, R, S, or deletion;

or f) wherein
X01=A, E, G, or deletion,
X02=C, D, E, diaminobutyric acid (Dab), diaminopropionic acid (Dpr), K, or ornithine (Orn),
X03=S or T,
X04=E, F, H, K, M, R, S, T, V, or Y,
X06=G, H, K, M, N, Q, or R,
X07=D;
X08=K,
X09=L,
X10=V,
X11=W,
X12=C, and
X13=T;
wherein
R$^1$=amino or acetyl and
R$^2$=COOH, amide, GK, GKK, (βA)GK, (βA)GKK (SEQ ID NO: 89), (βA)(βA), or (βA)(βA)K.

7. The peptide of claim 1, wherein the amino acid sequence is

R$^1$ CAWHLGKLVWC-R$^2$ (SEQ ID NO: 48),

R$^1$ CAWHLGKLVWCT R$^2$ (SEQ ID NO: 49),

R$^1$ DCAWHLGKLVWC R$^2$ (SEQ ID NO: 47),

R$^1$ DCAWHLGKLVWCT R$^2$ (SEQ ID NO: 56),

R$^1$ DCSWHLGKLVWCT R$^2$ (SEQ ID NO: 59),

R$^1$ DCAWHHGKLVWCT R$^2$ (SEQ ID NO: 50),

R$^1$ DCAWHQGKLVWCT R$^2$ (SEQ ID NO: 57),

R$^1$ DCAWHGGKLVWCT R$^2$ (SEQ ID NO: 52),

R$^1$ DCAWHGGKLVWCE R$^2$ (SEQ ID NO: 55),

R$^1$ DCAYHLGKLVWCT R$^2$ (SEQ ID NO: 58),

R$^1$ DCAYHQGKLVWCT R$^2$ (SEQ ID NO: 60),

R¹ DCSWHQGKLVWCT R² (SEQ ID NO: 61),

R¹ DCSYHLGKLVWCT R² (SEQ ID NO: 62),

R¹ DCSYHQGKLVWCT R² (SEQ ID NO: 63),

R¹-CAWHQGKLVWCT R² (SEQ ID NO: 65),

R¹-CAYHLGKLVWCT R² (SEQ ID NO: 66),

R¹-CSWHLGKLVWCT R² (SEQ ID NO: 67),

R¹-CAYHQGKLVWCT R² (SEQ ID NO: 68),

R¹-CSWHQGKLVWCT R² (SEQ ID NO: 69),

R¹-CSYHLGKLVWCT R² (SEQ ID NO: 70),

R¹-CSYHQGKLVWCT R² (SEQ ID NO: 71),

R¹ DCAWHQGKLVWC-R² (SEQ ID NO: 73),

R¹ DCAYHLGKLVWC-R² (SEQ ID NO: 74),

R¹ DCSWHLGKLVWC-R² (SEQ ID NO: 75),

R¹ DCAYHQGKLVWC-R² (SEQ ID NO: 76),

R¹ DCSWHQGKLVWC-R² (SEQ ID NO: 77),

R¹ DCSYHLGKLVWC-R² (SEQ ID NO: 78),

R¹ DCSYHQGKLVWC-R² (SEQ ID NO: 79),

R¹-CAWHQGKLVWC-R² (SEQ ID NO: 81),

R¹-CAYHLGKLVWC-R² (SEQ ID NO: 82),

R¹-CSWLGKLVWC-R² (SEQ ID NO: 83),

R¹-CAYHQGKLVWC-R² (SEQ ID NO: 84),

R¹-CSWHQGKLVWC-R² (SEQ ID NO: 85),

R¹-CSYHLGKLVWC-R² (SEQ ID NO: 86), or

R¹-CSYHQGKLVWC-R² (SEQ ID NO: 87), wherein
R¹=amino or acetyl and
R¹=COOH, amide, GK, GKK, (βA)GK, (βA)GKK (SEQ ID NO: 89), (βA)(βA), or (βA)(βA)K.

8. The peptide according to claim 1 in cyclic form, peptide ring formation being effected through:
1) disulfide bridging, between X02 and X12, when C=X02 and C=X12,
2) amide cyclization, between X02 and X12, when X02 is Dpr, Dab, K, or Orn in combination with D or E=X12,
3) amide cyclization, between X02 and X12, when X02 is D or E in combination with Dpr, Dab, K, or Orn=X12,
a) wherein
   X01=D,
   X02=C, D, E, diamninobutyric acid (Dab), diamninopropionic acid (Dpr), K, or ornithine (Orn),
   X03=A,
   X04=W,
   X06=L,
   X07=G,
   X08=K,
   X09=L,
   X10=V,
   X11=W,
   X12=C, and
   X13=deletion;
b) wherein
   X01=D,
   X02=C, D, E, diaminobutyric acid (Dab), diaminopropionic acid (Dpr), K, or ornithine (Orn),
   X03=A,
   X04=W,
   X06=L,
   X07=G,
   X08=K,
   X09=L,
   X10=V,
   X11=W,
   X12=C, S, D, E, diaminobutyric acid (Dab), diaminopropionic acid (Dpr), K, ornithine (Orn), and
   X13=T;
c) wherein
   X01=D,
   X02=C, D, E, diaminobutyric acid (Dab), diaminopropionic acid (Dpr), K, or ornithine (Orn),
   X03=S,
   X04=W,
   X06=L,
   X07=G,
   X08=K,
   X09=L,
   X10=V,
   X11=W,
   X12=C, S, D, E, diaminobutyric acid (Dab), diaminopropionic acid (Dpr), K, ornithine (Orn), and
   X13=T;
d) wherein
   X01=D,
   X02=C, D, E, diaminobutyric acid (Dab), diaminopropionic acid (Dpr), K, or ornithine (Orn),
   X03=A,
   X04=W,
   X06=H,
   X07=G,
   X08=K,
   X09=L,
   X10=V,
   X11=W,
   X12=C, S, D, E, diaminobutyric acid (Dab), diaminopropionic acid (Dpr), K, ornithine (Orn), and
   X13=T;
e) wherein
   X01=D,
   X02=C, D, E, diaminobutyric acid (Dab), diaminopropionic acid (Dpr), K, or ornithine (Orn),
   X03=A,
   X04=W,
   X06=Q,
   X07=G,
   X08=K,
   X09=L,
   X10=V,
   X12=W,
   X12=C, S, D, E, diaminobutyric acid (Dab), diaminopropionic acid (Dpr), K, ornithine (Orn), and
   X13=T;
f) wherein
   X01=D,
   X02=C, D, E, diaminobutyric acid (Dab), diaminopropionic acid (Dpr), K, or ornithine (Orn), X03=A,
X04=W,
X06=G,
X07=G,
X08=K,
X09=L,
X10=V,
X11=W,
X12=C, S, D, E, diaminobutyric acid (Dab), diaminopropionic avid (Dpr), K, or ornithine (Orn), and
X13=T;
g) wherein
X01=D,
X02=C, D, E, diaminobutyric acid (Dab), diaminopropionic acid (Dpr), K, or ornithine (Orn),
X03=A,
X04=W,
X06=G,
X07=G,
X08=K,
X09=L,
X10=V,
X11=W,
X12=C, S, D, E, diaminobutyric acid (Dab), diaminopropionic acid (Dpr), K, or ornithine (Orn), and
X13=E;
h) wherein
X01=D,
X02=C, D, E, diamninobutyric acid (Dab), diaminopropionic acid (Dpr), K, or ornithine (Orn),
X03=A,
X04=Y,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
i) wherein
X01=D,
X02=C, D, E, diaminobutyric acid (Dab), diaminopropionic acid (Dpr), K, or ornithine (Orn),
X03=A,
X04=Y,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
j) wherein
X01=D,
X02=C, D, E, diaminobutyric acid (Dab), diaminopropionic acid (Dpr), K, or ornithine (Orn),
X03=S,
X04=Y,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
k) wherein
X01=D,
X02=C, D, E, diaminobutyric acid (Dab), diaminopropionic acid (Dpr), K, or ornithine (Orn),
X03=S,
X04=Y,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
l) wherein
X01=D,
X02=C, D, E, diaminobutyric acid (Dab), diaminopropionic acid (Dpr), K, or ornithine (Orn),
X03=A,
X04=W,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
m) wherein
X01=deletion,
X02=C, D, E, diaminobutyric acid (Dab), diaminopropionic acid (Dpr), K, or ornithine (Orn),
X03=A,
X04=Y,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;
n) wherein
X01=deletion,
X02=C, D, E, diaminobutyric acid (Dab), diaminopropionic acid (Dpr), K, or ornithine (Orn),
X03=S,
X04=W,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=T;

o) wherein
  X01=deletion,
  X02=C, D, E, diaminobutyric acid (Dab), diaminopropionic acid (Dpr), K, or ornithine (Orn),
  X03=A,
  X04=Y,
  X06=G,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=T;
p) wherein
  X01=deletion,
  X02=C, D, E, diaminobutyric acid (Dab), diaminopropionic acid (Dpr), K, or ornithine (Orn),
  X03=S,
  X04=W,
  X06=Q,
  X07=G,
  X08=K,
  X09=L,
  X10=V,
  X11=W,
  X12=C, S, D, E, diaminobutyric acid (Dab), diaminopropionic acid (Dpr), K, ornithine (Orn), and
  X13=T;
q) wherein
  X01=deletion,
  X02=C, D, E, diaminobutyric acid (Dab), diaminopropionic acid (Dpr), K, or ornithine (Orn),
  X03=S,
  X04=Y,
  X06=L,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=T;
r) wherein
  X01=deletion,
  X02=C, D, E, diaminobutyric acid (Dab), diaminopropionic acid (Dpr), K, or ornithine (Orn),
  X03=S,
  X04=Y,
  X06=Q,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=T;
s) wherein
  X01=D,
  X02=C, D, E, diaminobutyric acid (Dab), diaminopropionic acid (Dpr), K, or ornithine (Orn),
  X03=A,
  X04=W,
  X06=Q,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=deletion;
t) wherein
  X01=D,
  X02=C, D, E, diaminobutyric acid (Dab), diaminopropionic acid (Dpr), K, or ornithine (Orn),
  X03=A,
  X04=Y,
  X06=L,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=deletion;
u) wherein
  X01=D,
  X02=C, D, E, diaminobutyric acid (Dab), diaminopropionic acid (Dpr), K, or ornithine (Orn),
  X03=S,
  X04=W,
  X06=L,
  X07=G,
  X08=K,
  X09=L,
  X10=V,
  X11=W,
  X12=C, S, D, E, diaminobutyric acid (Dab), diaminopropionic acid (Dpr), K, ornithine (Orn), and
  X13=deletion;
v) wherein
  X01=D,
  X02=C, D, E, diaminobutyric acid (Dab), diaminopropionic acid (Dpr), K, or ornithine (Orn),
  X03=A,
  X04=Y,
  X06=Q,
  X07=G,
  X08=K,
  X09=L,
  X10=V,
  X11=W,
  X12=C, S, D, E, diaminobutyric acid (Dab), diaminopropionic acid (Dpr), K, or ornithine (Orn), and
  X13=deletion;
w) wherein
  X01=D,
  X02=C, D, E, diaminobutyric acid (Dab), diaminopropionic acid (Dpr), K, or ornithine (Orn),
  X03=S,
  X04=W,
  X06=Q,
  X07=G,
  X08=K,
  X09=L, X10=V,
X11=W,
X12=C, S, D, E, diaminobutyric acid (Dab), diaminopropionic acid (Dpr), K, or ornithine (Orn), and
X13=deletion;

x) wherein
X01=D,
X02=C, D, E, diaminobutyric acid (Dab), diaminopropionic acid (Dpr), K, or ornithine (Orn),
X03=S,
X04=Y,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

y) wherein
X01=D,
X02=C, D, E, diaminobutyric acid (Dab), diaminopropionic acid (Dpr), K, or ornithine (Orn),
X03=S,
X04=Y,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

z) wherein
X01=deletion,
X02=C, D, E, diaminobutyric acid (Dab), diaminopropionic acid (Dpr), K, or ornithine (Orn),
X03=A,
X04=W,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

aa) wherein
X01=deletion,
X02=C, D, E, diaminobutyric acid (Dab), diaminopropionic acid (Dpr), K, or ornithine (Orn),
X03=A,
X04=Y,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

ab) wherein
X01deletion,
X02=C, D, E, diaminobutyric acid (Dab), diaminopropionic acid (Dpr), K, or ornithine (Orn),
X03=S,
X04=W,
X06=L,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

ac) wherein
X01=deletion,
X02=C, D, E, diaminobutyric acid (Dab), diaminopropionic acid (Dpr), K, or ornithine (Orn),
X03=A,
X04=Y,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion;

ad) wherein
X01=deletion,
X02=C, D, E, diaminobutyric acid (Dab), diaminopropionic acid (Dpr), K, or ornithine (Orn),
X03=S,
X04=W,
X06=Q,
X07=G,
X08=K,
X09=L,
X10=V,
X11=W,
X12=C, S, D, E, diaminobutyric acid (Dab), diaminopropionic acid (Dpr), K, or ornithine (Orn), and
X13=deletion; or ae) wherein
X01=deletion,
X02=C, D, E, diaminobutyric acid (Dab), diaminopropionic acid (Dpr), K, or ornithine (Orn),
X03=S,
X04=Y,
X06=L,
X07=G,
X08=K,
X09=L, X10=V,
X11=W,
X12=C, S, D, E, diaminobutyric acid (Dab), diaminopropionic acid (Dpr), K, ornithine (Orn), and
X13=deletion; or af) wherein
X01=deletion,
X02=C, D, E, diaminobutyric acid (Dab), diaminopropionic acid (Dpr), K, or ornithine (Orn),
X03=S,
X04=Y,
X06=Q,
X07=G,
X08=K,
X09=L,
X10=V,
X11=W,
X12=C, S, D, E, diaminobutyric avid (Dab), diaminopropionic acid (Dpr), K, or ornithine (Orn), and
X13=deletion;
wherein
$R^1$=amino or acetyl, and
$R^2$=COOH, amide, GK, GKK, (βA)GK, (βA)GKK (SEQ ID NO: 89), (βA)(βA), or (βA)(βA)K.

9. The peptide according to claim 1, characterized in that the peptide binds immunoglobulins or antigen-immunoglobulin complexes in biological fluids.

10. In a solid phase, for affinity chromatography or solid phase extraction, comprising:
a polymeric material; and
a peptide according to claim 1, wherein the peptide is immobilized on phase, whereby the peptide activates the volume material.

11. The solid phase according to claim 10, wherein the polymeric material comprises crosslinked agarose polymers, cellulose polymers, silica gel, polyamide, or polyvinyl alcohol.

12. The solid phase according to claim 11, wherein the peptide is covalently bound to the solid phase through the K(Lys) adjacent to X07.

13. A method for removing immunoglobulins from a sample, by affinity chromatography or solid phase extraction, comprising contacting an immunoglobulin-containing sample with the solid phase of claim 10, whereby the solid phase selectively binds immunoglobulins in the sample.

14. A method for removing immunoglobulins from a sample, by affinity chromatography or solid phase extraction, comprising contacting an immunoglobulin-containing sample with the solid phase of claim 12, whereby the solid phase selectively binds immunoglobulins in the sample.

15. The method of claim 13, wherein the immunoglobulin-containing sample is anticoagulant-treated human blood plasma or human whole blood.

16. The method of claim 14, wherein the immunoglobulin-containing sample is anticoagulant-treated blood plasma or human whole blood.

17. The method according to claim 13, wherein the immunoglobulins are autoantibodies related to an autoimmune disease.

18. The method according to claim 14, wherein the immunoglobulins are autoantibodies related to an autoimmune disease.

19. The method according to claim 17, wherein the autoimmune disease is a rheumatoid disease, multiple sclerosis, or myasthenia gravis.

20. The method according to claim 18, wherein the autoimmune disease is a rheumatoid disease, multiple sclerosis, or myasthenia gravis.

21. A device for removing immunoglobulins from an immunoglobulin-containing sample comprising the solid phase according to claim 11 in cooperation with means for entry of the immunoglobulin-containing sample to the solid phase.

* * * * *